(12) United States Patent
Hancock et al.

(10) Patent No.: US 7,666,433 B2
(45) Date of Patent: Feb. 23, 2010

(54) RECOMBINANT RSV STRAINS WITH ALTERED G PROTEIN

(75) Inventors: Gerald E. Hancock, New City, NY (US); Matthew B. Elliott, Branford, CT (US)

(73) Assignee: Wyeth Holdings Corporation, Madison, NJ (US)

( * ) Notice: Subject to any disclaimer, the term of this patent is extended or adjusted under 35 U.S.C. 154(b) by 283 days.

(21) Appl. No.: 11/629,609

(22) PCT Filed: Jun. 29, 2005

(86) PCT No.: PCT/US2005/023181

§ 371 (c)(1),
(2), (4) Date: Dec. 14, 2006

(87) PCT Pub. No.: WO2006/004874

PCT Pub. Date: Jan. 12, 2006

(65) Prior Publication Data

US 2007/0253977 A1 Nov. 1, 2007

Related U.S. Application Data

(60) Provisional application No. 60/584,092, filed on Jun. 30, 2004.

(51) Int. Cl.
| | | |
|---|---|---|
| *A61K 39/155* | (2006.01) |
| *A61K 39/295* | (2006.01) |
| *A61K 31/7105* | (2006.01) |
| *C12N 7/00* | (2006.01) |
| *C12N 7/01* | (2006.01) |
| *C12N 5/10* | (2006.01) |
| *C12N 15/86* | (2006.01) |
| *C12N 15/63* | (2006.01) |
| *C12N 15/45* | (2006.01) |

(52) U.S. Cl. .............. 424/199.1; 424/205.1; 424/211.1; 435/235.1; 435/236; 435/320.1; 435/325; 435/69.3; 536/23.72; 514/44 R

(58) Field of Classification Search ........................ None
See application file for complete search history.

(56) References Cited

U.S. PATENT DOCUMENTS 6,699,478 B1 * 3/2004 Hancock et al. .......... 424/211.1

FOREIGN PATENT DOCUMENTS

WO WO99/14334 * 3/1999

OTHER PUBLICATIONS

Hancock et al (Journal of Infectious Diseases 184:1589-93, 2001; in IDS).*
Hancock et al (Journal of Medical Virology 70:301-308, 2003; in IDS).*
Sparer et al (Journal of Experimental Medicine 187:1921-1926, 1998; in IDS).*
Elliott et al (Journal of Virology 78: 5773-5783, 2004; in IDS).*
Teng et al (Journal of Virology 76:6164-6167, 2002; in IDS).*
Teng et al (Virology 289:283-296, 2001; in IDS).*
Haynes et al (Journal of Virology 77:9831-9844, 2003).*
Anderson, L. et al., J. Virol., 62, 4232-4238, (1988).
Bendelja, K. et al., Clin. Exp. Immunol., 121, 332-338, (2000).
Bui, R. et al., J. Pediatr., 110, 87-90, (1987).
Bukreyev, A. et al., J. Virol., 71, 8973-8982, (1997).
Chen, M. et al., J. Immunol., 169, 3208-3216, (2002).
Collins, P. et al., J. Virol., 49, 572-578, (1984).
Crowe, J. et al., Vaccine, 12, 783-790, (1994).
Davies, D. et al., J. Allergy Clin. Immunol., 111,215-225, (2003).
Elliott, M. et al., J.Virol., 78, 5773-5783, (2004).
Firestone, C. et al., Virology, 225, 419-422, (1996).
Friedewald, W. et al., J.A.M.A., 204(8), 690-694, (1968).
Fuhlbrigge, A. et al., Am. J. Respir. Crit. Care Med., 166, 1044-1049, (2002).
Graham, B. et al., Immunopharmacology, 48, 237-247, (2000).
Hancock, G. et al., J. Infect. Dis., 181, 1768-1771, (2000).
Hancock, G. et al., J. Infect. Dis., 184, 1589-1593, (2001).
Hancock, G. et al., J. Med. Virol., 70, 301-308, (2003).
Hancock, G. et al., Vaccine, 13 (4), 391-4000, (1995).
Hancock, G. et al., Vaccine, 21, 4348-4358, (2003).
Holt, P., Am. J. Respir. Crit. Care Med., 161, S172-S175, (2000).
Huang. Y., J. Virol. 46 (2), 667-672, (1983).
Hull, J. et al., Thorax, 55, 1023-1027, (2000).
Jackson, M., J. Med. Virol., 49, 161-169, (1996).
Kapikian, A. et al., Am. J. Epidemiol, 89 (4), 405-421, (1969).
Kim, H. et al., Am. J. Epidemiol, 89 (4), 422-434, (1969).
Kim, H. et al., Pediat. Res., 10, 75-78, (1976).
Kim, H. et al., Pediatrics, 48 (5), 745-755, (1971).
Kneyber, M., Pediatr. Infect. Dis. J., 21 (7), 685-696, (2002).
Larche, M. et al., J. Allergy Clin. Immunol., 111 (3), 450-463, (2003).
Lemanske, R., Pediatr Allergy Immunol., 13 (Suppl. 15), 38-43, (2002).
Martinez, F., Pediatr Infect Dis. J., 22, S76-S82, (2003).
Murphy, B., J. Clin. Invest., 110, 21-27, (2002).
Openshaw, P. et al., Int. Immunol., 4, 493-500, (1992).
Piedra, P., Pediatr. Infect. Dis. J., 22, S94-S99, (2003).
Rabatic, S. et al., J. Infect. Dis., 175, 32-37, (1997).
Renzi, P. et al., J. Pediatr., 130, 584-593, (1997).
Roman, M. et al., Am. J. Respir. Crit. Care Med., 156, 190-195, (1997).

(Continued)

*Primary Examiner*—Mary E Mosher
(74) *Attorney, Agent, or Firm*—Gloria K. Szakiel; Alan M. Gordon

(57) ABSTRACT

The construction of recombinant respiratory syncytial virus (RSV) strains deleted of the region of G protein most likely to induce unwanted type 2 T cell responses in susceptible recipients is disclosed. Using reverse genetics, recombinant RSV strains were engineered with deletions of amino acids 151-221 and 178-219. Both RSV strains replicated in the respiratory tract of BALB/c mice and elicited serum neutralization and anti-F protein IgG titers that were equivalent to cp-RSV and contributed to a 3.9 $\log_{10}$ reduction in RSV A2 four days after challenge. Importantly, pulmonary eosinophilia was significantly diminished in BALB/c mice primed with native G protein and challenged with either recombinant RSV strain. These findings are important for the development of immunogenic compositions against RSV.

48 Claims, 7 Drawing Sheets

OTHER PUBLICATIONS

Shay, D. et al., JAMA, 282 (15), 1440-1446, (1999).
Sigurs, N., Paediatr. Respir. Rev., 3, 177-183, (2002).
Sparer, T. et al., J. Exp. Med., 187 (11), 1921-1926, (1998).
Sullender, W., Virology, 209, 70-79, (1995).
Tebbey, P. et al., J. Exp. Med., 188 (10), 1967-1972, (1998).
Techaarpornkul, S. et al., J. Virol., 75 (15), 6825-6834, (2001).
Teng, M., J.Virol., 76(12), 6164-6171, (2002).
Teng, M. et al., Virology, 289, 283-296 (2001).
Varga, S. et al., J. Immunol., 165, 6487-6495, (2000).
Welliver, R., Pediatr Infect Dis. J., 22, S6-S12, (2003).
Whitehead, S. et al., J. Virol., 73 (4), 3438-3442, (1999).
Wright, P. et al., Arch. Gesamte Virusforsch., 41, 238-247, (1973).

* cited by examiner

FIG. 6

RECOMBINANT RSV STRAINS WITH ALTERED G PROTEIN

This application is the US national phase of international application PCT/US2005/023181 filed on Jun. 29, 2005, which designated the US and claims priority to U.S. Provisional Application No. 60/584,092, filed on Jun. 30, 2004. The entire contents of these applications are incorporated herein by reference.

FIELD OF THE INVENTION

This invention relates to isolated, recombinantly-generated, respiratory syncytial virus strains comprising defined deletions in the external domain corresponding to amino acids 151 to 221 of the G protein. These deletions significantly diminish the unbalanced type 2 T cell responses that lead to pulmonary eosinophilia.

BACKGROUND OF THE INVENTION

Respiratory syncytial virus (RSV) is a non-segmented, negative strand RNA virus of the Order designated Mononegavirales. Specifically, RSV is a member of the family Paramyxoviridae, genus *Pneumovirus* (1, 2). Respiratory tract disease caused by RSV imposes a significant burden on healthcare and all age groups are infected. The most significant disease however, occurs in young infants, aged adults, and patients with immunological abnormalities. It is estimated that lower respiratory tract (LRT) disease caused by RSV is responsible for 90% of bronchiolitis in infancy and 50% of all cases of pneumonia during the first two years of life. Thus, there is an urgent need for immunogenic compositions against RSV. Both subunit and live-attenuated immunogenic composition strategies have been followed to prevent LRT disease (3, 4). Unfortunately, neither tactic has thus far produced an acceptable product. The recent advent of "reverse genetics" technology, however, brings great promise for future immunogenic compositions (5). With "reverse genetics," recombinant RSV strains may be genetically engineered with defined mutations to ensure an attenuated phenotype, or include genes encoding cytokines to modify adaptive immune responses. One caveat, however, is that replication of recombinant RSV in the airways may generate inflammatory responses that lead to wheezing in susceptible infants and toddlers. It is well documented that RSV bronchiolitis is a major risk factor for wheeze up to age 13 (6) and it is even suggested to set in motion immunological events that contribute to asthma (7).

The exact mechanisms whereby RSV infection brings about wheeze and asthma-like symptoms are unknown. It is likely that both innate and adaptive immune responses are involved. Several reports suggested that type 2 T cell responses were dominant in human infants with LRT disease caused by RSV. Peripheral blood eosinophilia, RSV-specific IgE and IgG4, and increased secretion of IL-4 from peripheral blood mononuclear cells (PBMC) stimulated with allergen or mitogen were associated with acute bronchiolitis caused by RSV (8, 9, 10). Because type 2 T cell responses and atopy are, key factors in asthma (11), unbalanced T cells responses against RSV antigens could contribute to harmful airway inflammation.

An antigen of primary interest in eliciting unbalanced T cell responses is the RSV attachment (G) protein. G protein is a heavily glycosylated 90-kDa type II transmembrane protein that is synthesized in both secreted and membrane-bound forms and has an important role in attachment of RSV to the host cell. The findings from several laboratories established that immunization with highly purified native or vaccinia virus-expressed recombinant G protein primed naïve BALB/c mice for pulmonary eosinophilia upon subsequent challenge with infectious RSV (12, 13). Eosinophilia was dependent on the presence of IL-5 and $CD4^+$ T cells. In contrast, immunization with vaccinia virus-expressed RSV fusion (F) protein (12, 13), or appropriately adjuvanted natural F protein (14), did not prime for eosinophilia. Therefore, it may be possible to increase the safety profile of live attenuated immunogenic compositions or heterologous-expressed antigens of RSV through identification and deletion of G protein antigens that contribute to type 2 T cell responses. These antigens were identified in four inbred strains of naïve mice following immunization with native G protein (15). In a majority of strains, the responsible epitopes were located within the ectodomain encompassed by amino acids 149 to 200. Peptide-mapping studies further revealed that PBMC from most human donors readily recognized T cell epitopes present in amino acids 149 to 200 of G protein (16).

SUMMARY OF THE INVENTION

Accordingly, the present invention pertains to the construction and characterization of recombinantly-generated respiratory syncytial virus (RSV) strains deleted of the region of G protein most likely to induce unwanted T cell responses in a vertebrate. More particularly, the present invention pertains to an isolated, recombinantly-generated respiratory syncytial virus (RSV) strain comprising at least one alteration in the region corresponding to amino acids 151-221 of the RSV G protein, wherein the alteration is a deletion of at least amino acids 178-219, but not more than a deletion of amino acids 151-221. In one embodiment, the deletion in the altered G protein consists of amino acids 151 to 221. In another embodiment, the deletion in the altered G protein consists of amino acids 178 to 219.

The invention also pertains to an immunogenic composition comprising an isolated, recombinantly-generated respiratory syncytial virus (RSV) strain comprising at least one alteration in the region corresponding to amino acids 151-221 of the RSV G protein, wherein the alteration is a deletion of at least amino acids 178-219, but not more than a deletion of amino acids 151-221, together with a physiologically acceptable diluent or carrier. In one embodiment, the immunogenic composition further comprises an adjuvant.

The invention further pertains to a method of immunizing a vertebrate against RSV, which comprises administering to the vertebrate the immunogenic compositions just described.

The invention also relates to an isolated, altered G protein or polypeptide of RSV, comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV. In one embodiment, the enhanced disease is atypical pulmonary inflammation, particularly pulmonary eosinophilia.

The invention also relates to an immunogenic composition comprising a physiologically acceptable diluent or carrier and an isolated, altered G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV. In one embodiment, the immunogenic composition further comprises an adjuvant. In another embodiment, the immunogenic composition further comprises isolated F protein of RSV. In yet another embodiment, the immunogenic composition further comprises isolated M protein of RSV. And in still another embodiment, the immunogenic composition further comprises isolated F protein of RSV and isolated M protein of RSV.

The invention also relates to a method of immunizing a vertebrate against RSV, comprising administering to the vertebrate a composition comprising an immunologically effective amount of an isolated, altered G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into the immunogenic composition and administered to a vertebrate, does not induce enhanced disease upon subsequent infection of the vertebrate with RSV. In one embodiment, the composition further comprises an immunologically effective amount of isolated F protein of RSV. In another embodiment, the composition further comprises an immunologically effective amount of isolated M protein of RSV. In yet another embodiment, the composition further comprises immunologically effective amounts of isolated F protein of RSV and isolated M protein of RSV. In another embodiment, the vertebrate is a seronegative human.

The invention further relates to an isolated nucleic acid molecule encoding an altered G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV.

The invention further relates to an expression vector comprising this isolated nucleic acid molecule operably linked to a regulatory sequence.

The invention further relates to a chimeric expression vector comprising:

a) an isolated nucleic acid molecule encoding an altered G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV;

b) an isolated nucleic acid molecule encoding all or an immunogenic portion of F protein of RSV; and c) a regulatory sequence operably linked to both (a) and (b).

The invention further relates to a recombinant host cells comprising these expression vectors.

The invention further relates to a method of producing an altered G protein or polypeptide of RSV, which comprises at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV, the method comprising maintaining the recombinant host cell described above under conditions suitable for expression of the altered G protein or polypeptide.

The invention further relates to a method of producing a chimeric polypeptide comprising an altered G protein or polypeptide of RSV, which comprises at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV, and all or an immunogenic portion of F protein of RSV, the method comprising maintaining the recombinant host cell described above under conditions suitable for expression of the encoded chimeric protein.

The invention further relates to an immunogenic composition comprising a physiologically acceptable diluent or carrier and an isolated nucleic acid molecule encoding an altered G protein or polypeptide of RSV, which comprises at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when expressed by the immunogenic composition upon administration to a vertebrate, does not induce enhanced disease upon subsequent infection of the vertebrate with RSV. In one embodiment, the immunogenic composition further comprises a transfection-facilitating agent.

The invention further relates to a method of immunizing a vertebrate against RSV, comprising administering to the vertebrate a composition comprising an immunologically effective amount of an isolated, nucleic acid molecule encoding an altered G protein or polypeptide of RSV, and a transfection-facilitating agent, wherein said altered G protein or polypeptide of RSV comprises at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when expressed by the immunogenic composition upon administration to the vertebrate, does not induce enhanced disease upon subsequent infection of the vertebrate with RSV. In one embodiment, the vertebrate is a seronegative human.

The invention also relates to an immunogenic composition comprising a physiologically acceptable diluent or carrier and an immunologically effective amount of a live attenuated pathogen that has inserted within it as a heterologous nucleic acid segment, a nucleic acid sequence encoding an altered G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, such that upon administration to the vertebrate, the altered G protein or polypeptide is expressed and is immunogenic, but does not induce enhanced disease upon subsequent infection of the vertebrate with RSV. In one embodiment, the live attenuated pathogen is an attenuated virus, such as, for example, an alphavirus such as Venezuelan equine encephalitis virus (VEEV). In another embodiment, the attenuated pathogen is an attenuated virus, such as a non-segmented negative strand RNA virus of the Order designated Mononegavirales. Examples of Mononegavirales include vesicular stomatitis virus (VSV), parainfluenza viruses, measles virus, mumps virus and human metapneumovirus.

BRIEF DESCRIPTION OF THE FIGURES

FIG. 6 depicts eosinophilia in the lungs of native G protein sensitized mice after challenge with rRSV. BALB/c (H2$^d$) and C57Bl/6 (H2$^b$) mice were injected intramuscularly on weeks 0 with native G protein (1.μg/dose) prepared in PBS alone. The mice were challenged with the indicated virus two weeks after the last injection and pulmonary eosinophilia (±.1 standard deviation) was assessed seven days thereafter. Eosinophilia was significantly (p<0.05) reduced in BALB/c mice challenged with the rRSV. The asterisk denotes control mice immunized with native G protein admixed with CpG oligonucleotide adjuvant (100.μg/dose) and challenged with cp-RSV strain of RSV. There were five mice per group.

DETAILED DESCRIPTION OF THE INVENTION

Figure 1:
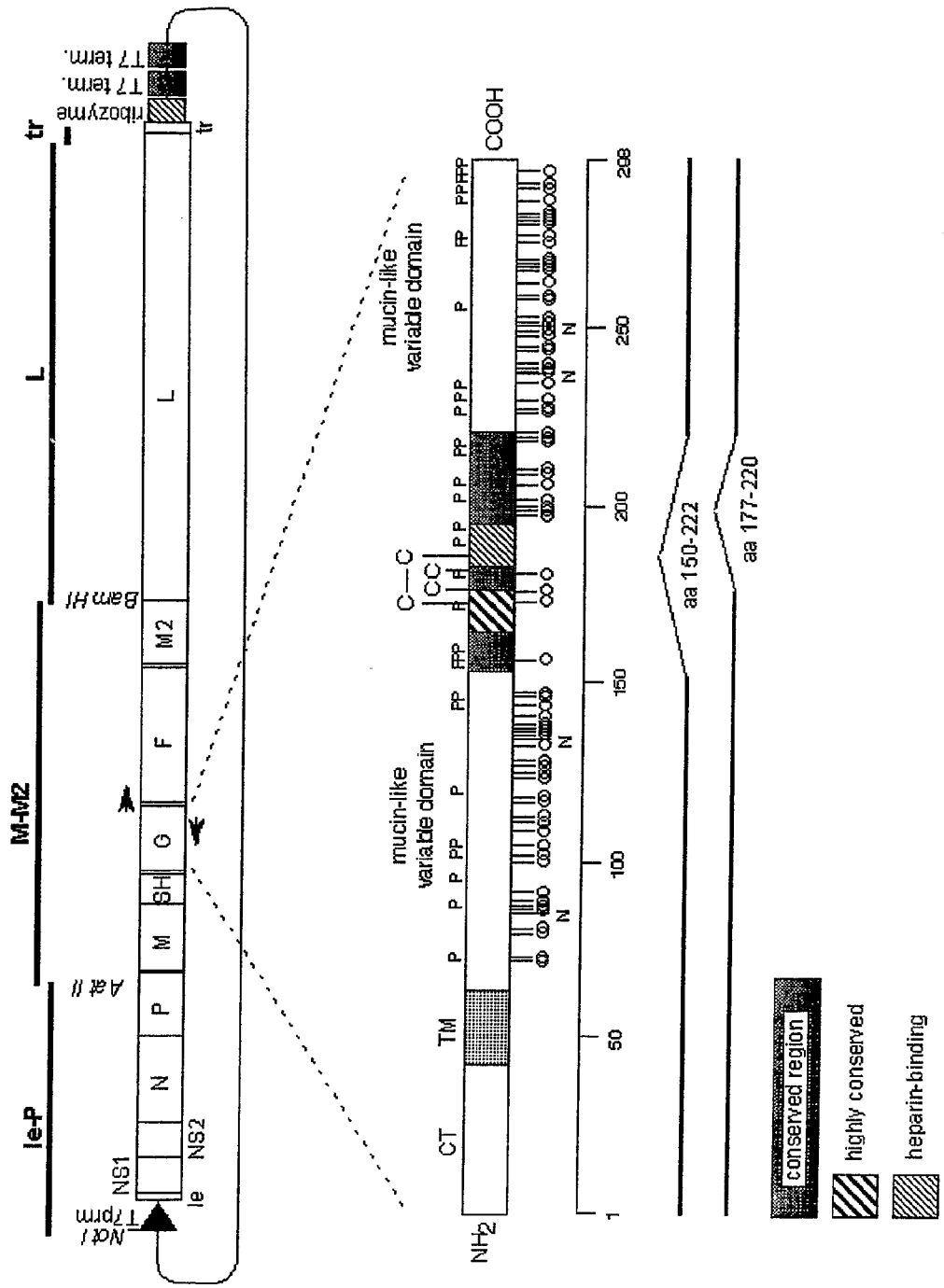
FIG. 1 depicts the construction of rRSV antigenomic cDNA with altered G protein. The plasmid pFL M-M2 containing genes encoding M, SH, G, F, and M2 proteins of RSV was genetically altered by PCR mutagenesis to exclude nucleotides corresponding to amino acids 151-221 (the nucleotide sequence encoding amino acids 151-221 is SEQ ID NO:1; the sequence of amino acids 151-221 is SEQ ID NO:2) or 178-219 (the nucleotide sequence encoding amino acids 178-219 is SEQ ID NO:3; the sequence of amino acids 178-219 is SEQ ID NO:4) of G protein from amplification. The resultant plasmids were then combined with other rRSV plasmids and transfected into Vero cells. The resulting rRSV strains were respectively labeled rA2cpΔG150-222 (so designated because the G protein contains amino acids up through 150 and commencing again with amino acid 222) and rA2cpΔG177-220 (so designated because the G protein contains amino acids up through 177 and commencing again with amino acid 220). G gene regimes include CT, cytoplasmic tail; TM, transmembrane region; P, proline residues; C, cysteine residues; stalks with circles, potential O-linked carbohydrate acceptor sites; N, potential N-linked carbohydrate acceptor sites.

Asthma is a chronic inflammatory disease of the airways and characterized by inflammation, hyper reactive airways, bronchial obstruction, and recurrent episodes of wheezing. In severe cases asthma is also distinguished by significant airway remodeling (17). Asthma imposes a substantial burden on societies worldwide. In the United States alone, the incidence of asthma increased dramatically in the past 20 years, especially among children less than five years of age where the rate increased approximately 160% (18). For many individuals asthma becomes evident within the first few years of life. Although the precipitating events are not fully understood, both genetic (17, 19) and environmental factors are likely involved. Regarding environmental factors, there is increased interest in LRT disease caused by RSV (20). LRT disease in infancy caused by RSV places pediatric populations at increased risk for persistent wheezing and asthma-like symptoms until age 13 (6). Indeed, the increased incidence of hospitalizations related to RSV bronchiolitis during the past two decades is similar to the upsurge in asthma (21). Thus, a successful prophylactic immunogenic composition for RSV would not only lessen disease and prevent hospitalizations caused by acute bronchiolitis, but also significantly diminish wheezing illnesses (and possibly asthma) from infancy through adolescence.

Two issues confront successful development of RSV immunogenic compositions for naïve infants. The immunogenic composition must be sufficiently immunogenic in the presence of maternal antibody to be efficacious, yet not predispose the recipient for immunopathology in the airways. Both subunit and attenuated RSV immunogenic composition strategies are currently being pursued. For highly purified protein-based or vectored subunit immunogenic compositions, the putative attachment G and fusion (F) proteins are of primary interest. Both proteins are located in the envelope and are major protective antigens. Hence, immunization with combination subunit immunogenic compositions containing both antigens would likely generate more efficacious immune responses (22, 23). It is critical, however, that subunit immunogenic compositions do not elicit unbalanced adaptive immune responses that are primarily composed of type 2 T cells. The enhanced disease observed in RSV-naïve human infants administered formalin-inactivated immunogenic compositions (24, 25) was associated with immune responses that were unbalanced and dominated by type 2 T cells (12, 26). Asthma is associated with type 2 T cells and atopy (11). The dominance of type 2 T cells in naïve rodents can be overcome through formulation of highly purified proteins with adjuvants that target toll-like receptors (27). However, for vectors such as vaccinia virus, type 2 T cell responses against G protein remained dominant (13). Only alphavirus RNA replicons encoding F and G proteins elicited balanced T cell responses following intranasal administration to naïve rodents (28). When the replicons were injected subcutaneously, however, pulmonary pathology was still observed. Thus for subunit or vectored immunogenic compositions, special measures are required to ensure generation of balanced T cell responses.

Great care must also be exercised in designing safe and efficacious attenuated RSV immunogenic compositions. Finding the appropriate level of attenuation for naïve infants without sacrificing immunogenicity, and ensuring no reversion to a less attenuated phenotype is not without complication. In addition, infants are prone to generate T cell responses in the first few months of life that are type 2 in nature, presumably because of the T-helper 2 (Th2) cytokine-enriched environment in utero (39). Type 2 T cell responses were observed in infants with LRT disease caused by RSV (29, 10, 30, 31). Elevated serum IgE levels and peripheral blood eosinophilia at the time of RSV infection were further associated with asthma (32). Thus, immune responses following infection with an attenuated virus of limited replication could in the susceptible recipient induce responses that are unbalanced and primarily composed of type 2 T cells.

Presented herein is the work done to increase the safety profile of attenuated immunogenic compositions through the construction of recombinant RSV strains deleted of 42 (residues 178 to 219) or 71 (residues 151-221) amino acids in the central ectodomain of G protein. The recombinant RSV strains were respectively designated rA2cpΔG177-220 (SEQ ID NOS:3 and 4) and rA2cpΔG150-222 (SEQ ID NOS:1 and 2). The strategy was based upon results from studies that indicated PBMC from most adult human donors were readily activated upon stimulation with peptide antigens from the region of G protein spanned by amino acids 149-200 (16). It was further demonstrated that epitopes within the region primed several inbred strains of mice for pulmonary eosinophilia (15). Initially, it was unclear what impact genetic alteration of this magnitude would have on attenuation, immunogenicity, and pulmonary eosinophilia. Studies demonstrated that a recombinant RSV strain deleted of 26 amino acids containing the highly conserved cysteine noose could be rescued (recovered by reverse genetics) without adverse effects on replication (33). Indeed, a recombinant RSV strain completely deleted of G protein was successfully rescued (34, 35). However, the complete absence of G protein severely restricted replication in vivo. This recombinant RSV ΔG strain was thus overly attenuated and limited the potential use of this strain as an immunogenic composition. Alternatively, efficacious immunity was observed (36) following immunization of BALB/c mice with vaccinia virus-expressed G protein altered by frame-shift in the region shown to be responsible for eosinophilia (37, 38). Following challenge with the Long strain of RSV, eosinophilia was not observed.

The results presented herein extend these previous observations and demonstrate that a recombinant RSV strain with 71 amino acids removed from the central ectodomain can be rescued and replicate without significant restriction. The recombinant RSV strains were not sensitive to physiologic temperature and replicated as well as cp-RSV in vivo. Positive reactivity with monoclonal antibodies suggested that deletion of the central ectodomain in addition, did not significantly alter the structure of the C-terminal one third of G protein. The recombinant RSV strains as immunogenic compositions were immunogenic and elicited efficacious immune responses. Most importantly, upon challenge of native G protein primed BALB/c mice with rA2cpΔG177-220 or rA2cpΔG150-222, pulmonary eosinophilia was significantly diminished. Thus, the potential of these recombinant RSV strains to elicit dominant type 2 responses was significantly lessened without apparent loss of immunogenicity.

The substitution of wild type genes with ones encoding genetically altered G proteins from both A and B strains of RSV will facilitate the development of subunit immunogenic compositions, as well as strategies based upon attenuated strains of RSV. Importantly, the risk for inducing unbalanced T cell responses in naïve populations will be inherently less.

Specifically, the work described herein is directed to generating altered versions of the G protein of RSV which are less likely to induce dominant type 2 T cell responses, recombinant RSV strains containing one or more of such alterations, and immunogenic compositions containing such recombinant RSV strains. The strategy involves making at least one alteration in the region corresponding to amino acids 151-221 of the RSV G protein, wherein the alteration is a deletion of at least amino acids 178-219, but not more than a deletion of amino acids 151-221, which results in a protein or polypeptide derived from RSV G protein that is immunogenic without priming for atypical pulmonary inflammation (e.g., pulmonary eosinophilia) or any form of enhanced RSV disease.

The wild type (native) nucleotide and amino acid sequences of the RSV G protein are known in the art (Wertz et al., Proc. Natl. Acad. Sci. USA 92:4075-4079 (1985); Satake et al., Nucl. Acids Res. 13(21): 7795-7810 (1985)). As used herein, "alteration" and its derivatives is intended to mean an amino acid sequence which is different from the wild-type sequence, as well as a nucleotide sequence which encodes an amino acid sequence which is different from the wild-type amino acid sequence. Alteration includes insertion, deletion and/or substitution of one or more nucleotides or amino acids.

For example, the alteration(s) can preserve the three-dimensional configuration of the native G protein. Moreover, amino acids that are essential for the function of the G protein, particularly for immunogenicity, can be identified by methods known in the art. Particularly useful methods include identification of conserved amino acids, site-directed mutagenesis and alanine-scanning mutagenesis (for example, Cunningham and Wells, Science 244:1081-1085 (1989)), crystallization and nuclear magnetic resonance. The altered polypeptides produced by these methods can be tested for particular biologic activities, including immunogenicity, reduction in pulmonary eosinophilia and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (Science 247:1306-1310 (1990)).

Although this invention is exemplified by altered G proteins having deletions of the regions 151-221 or 178-219 or any part thereof, with continued use of the remaining RSV G protein derived moiety, other alterations of the wild type residues are also within the scope of this invention. In particular, deletions intermediate in size to the two deletions are contemplated. Such alterations retain attributes of the region of the G protein involved in protective immune responses but delete or modify epitopes involved in the generation of T cell responses that lead to pulmonary eosinophilia (i.e., a biological equivalent). Deletions can be replaced by linker regions that retain the spatiality of the remaining G protein or polypeptide in order for optimal translation and/or immunogenicity. Alterations can be made using any standard mutagen or mutagenic process, such as site-directed mutation involving phages or use of polymerase chain reaction (PCR) technology involving synthetic oligonucleotides. For example, DNA primers are designed which are complementary to the genomic RNA sequence to be deleted, based on the wild-type nucleotide sequence described above in Wertz et al. (1985).

Accordingly, the invention pertains to a nucleotide sequence encoding an altered G protein of RSV, or portion thereof, wherein the altered G protein or portion thereof retains immunogenicity. As used herein, the term "altered G protein" is intended to mean a G protein (or portion thereof) of RSV that retains immunogenicity and which, when incorporated into an immunogenic composition and administered to a vertebrate, does not induce enhanced disease (e.g., atypical pulmonary inflammation, such as pulmonary eosinophilia) upon subsequent infection with RSV. In a particular embodiment, the altered G protein comprises at least one alteration in the region corresponding to amino acids 151-221 of the RSV G protein, wherein the alteration is a deletion of at least amino acids 178-219, but not more than a deletion of amino acids 151-221.

Although the invention is specifically described with relation to the regions of RSV G protein comprising amino acids 151-221 and 178-219, it is intended that the methodologies described herein used to identify these regions can be applied to additional regions of the wild-type G protein to identify additional regions for alteration. For example, the regions upstream (toward the amino-terminus) and downstream (toward the carboxy-terminus) of the studied amino acid region (149-200) can be analyzed for additional domains in which alteration will produce beneficial effects. Alternatively, the region of amino acids from 149 to 200 can be re-analyzed with peptides having different overlaps to identify other domains in which alteration would be beneficial.

The term "nucleotide sequence" can include a nucleotide sequence that is synthesized chemically or by recombinant means. Thus, recombinant DNA contained in a vector is included in the invention. Also, nucleotide sequences include recombinant DNA molecules in heterologous host cells (including live attenuated viruses or virus replicons), as well as partially or substantially purified DNA molecules in solution. In vivo and in vitro RNA transcripts of the DNA molecules of the present invention are also encompassed by nucleotide sequences of the invention. Such nucleotide sequences are useful, e.g., in the manufacture of the encoded altered G protein.

The invention also encompasses variations of the nucleotide sequences of the invention, such as those encoding portions, analogues or derivatives of the altered G protein, provided the portion, analogue or derivative comprises the altered G protein. Such variations can be naturally occurring variations in the unaltered portion of the nucleotide sequence, such as in the case of allelic variation, or non-naturally occurring, such as those induced by various mutagens and mutagenic processes. Intended variations include, but are not limited to, addition, deletion and substitution of one or more nucleotides that can result in conservative or non-conservative amino acid changes, including additions and deletions.

The invention also pertains to nucleotide sequences that hybridize under medium and high stringency hybridization conditions (e.g., for selective hybridization) to a nucleotide sequence described herein. Appropriate stringency conditions are known to those skilled in the art or can be found in standard texts such as Current Protocols in Molecular Biology, John Wiley & Sons, N.Y. (1989), 6.3.1-6.3.6.

Accordingly, the invention pertains to nucleotide sequences which have a substantial identity with the altered nucleotide sequences described herein, such as, for example, at least about 90% identity or at least about 95% identity with these sequences. Particular nucleotide sequences encode polypeptides having substantially similar immunogenic activity as the altered G protein described herein. This invention also pertains to an altered G protein or polypeptide of RSV. The altered G protein or polypeptide is a G protein (or portion thereof) of RSV which retains immunogenicity and which, when incorporated into an immunogenic composition and administered to a vertebrate, does not induce enhanced disease (e.g., atypical pulmonary inflammation such as pulmonary eosinophilia) upon subsequent infection with RSV. In a particular embodiment, the altered G protein comprises at least one alteration in the region corresponding to amino acids 151-221 of the RSV G protein, wherein the alteration is a deletion of at least amino acids 178-219, but not more than a deletion of amino acids 151-221. The altered G protein of the invention is substantially purified (e.g., purified to homogeneity), and is substantially free of other proteins.

The altered G protein or polypeptide can also be a fusion protein comprising all or a portion of the altered G protein amino acid sequence fused to an additional component. Additional components, such as radioisotopes and antigenic tags, can be selected to assist in the isolation or purification of the polypeptide or to extend the half-life of the polypeptide; for example, a hexahistidine tag would permit ready purification by nickel chromatography. Alternatively, the altered G protein or polypeptide can be a fusion protein comprising all or a portion of the altered G protein amino acid sequence fused to all or a portion of the RSV F protein amino acid sequence (Collins et al., Proc. Natl. Acad. Sci. (USA) 81:7683-7687 (1984); U.S. Pat. No. 5,639,853; U.S. Pat. No. 5,723,130).

The invention also includes altered G proteins and polypeptides which comprise additional amino acid alterations beyond those alterations necessary to prevent production of enhanced disease in a vertebrate to which the altered protein or polypeptide is administered. For example, amino acid alterations, e.g., conservative amino acid changes that do not impact on the disease characteristics resulting from administration of the altered protein are included in the invention. Also included in the invention are polypeptides which are at least about 70% identical to the altered G protein or polypeptide described herein. However, polypeptides exhibiting lower levels of identity are also useful, particular if they exhibit high, e.g., at least about 70%, identity over one or more particular domains of the protein. For example, altered polypeptides sharing high degrees of identity over domains necessary for particular activities, including immunogenic function and receptor binding activity, are included herein. Polypeptides described herein can be chemically synthesized or recombinantly produced.

The invention also provides expression vectors, e.g., nucleic acid constructs, containing a nucleic acid sequence encoding an altered G protein or polypeptide, operably linked to at least one regulatory sequence. Many such vectors are commercially available, and the skilled artisan can readily prepare other suitable vectors. "Operably linked" is intended to mean that the nucleotide sequence is linked to a regulatory sequence in a manner which allows expression of the nucleic acid sequence; this term is intended to include both direct physical linkage and linkage by means of a linker or intervening sequence. Regulatory sequences are art-recognized and are selected to produce a polypeptide that is an altered G protein or polypeptide. Accordingly, the term "regulatory sequence" includes promoters, enhancers, and other expression control elements which are described in Goeddel, Gene Expression Technology: Methods in Enzymology 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed.

For instance, the altered G proteins and polypeptides of the present invention can be produced by ligating the nucleic acid molecule, or a portion thereof, into a vector suitable for expression in either prokaryotic cells, eukaryotic cells or both (see, for example, Broach, et al., Experimental Manipulation of Gene Expression, ed. M. Inouye (Academic Press, 1983) p. 83; Molecular Cloning: A Laboratory Manual, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

The expression construct can comprise a regulatory sequence operably linked to a nucleic acid molecule encoding an altered G protein or polypeptide, optionally linked, either directly or by means of a polynucleotide linker, to a nucleic acid molecule encoding all or a portion of the RSV F protein. Expression of such an expression construct will result in a chimera comprising an altered G protein or polypeptide and all or a portion of an F protein or polypeptide; if a polynucleotide linker is utilized in the construct, the F and altered G polypeptides will be linked by one or more amino acids. Methods for preparing and expressing F/G chimeras in general are taught, e.g., in U.S. Pat. No. 5,194,595 (Wathen), the teachings of which are incorporated herein by reference.

Prokaryotic and eukaryotic host cells transfected by the described vectors are also provided by this invention. For instance, cells which can be transformed, transfected or infected with the expression vectors of the present invention include, but are not limited to, bacterial cells such as E. coli (e.g., E. coli K12 strains), Streptomyces, Pseudomonas, Serratia marcescens and Salmonella typhimurium, insect cells (baculovirus), including Drosophila, Sf9 and Sf21 cells, fungal cells, such as yeast cells, plant cells and mammalian cells, such as thymocytes, Chinese hamster ovary (CHO) cells, HEp-2 cells, Vero cells and COS cells.

Thus, a nucleotide sequence encoding the altered G protein or polypeptide described herein can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect, plant or mammalian) or prokaryotic (bacterial cells), are standard procedures used in producing other well-known proteins. Viral vectors include, but are not limited to, adenoviruses, adeno-associated viruses, herpes simplex virus, retroviruses, lentiviruses, poxviruses, including vaccinia virus, alphaviruses, such as sindbis virus, Semliki forest virus, and Venezuelan equine encephalitis virus, and non-segmented, negative-stranded RNA viruses, such as measles virus, mumps virus, parainfluenza viruses (such as parainfluenza virus type 1 (PIV-1), parainfluenza virus type 2 (PIV-2), and human or bovine parainfluenza virus type 3 (hPIV-3 or bPIV-3)), human metapneumovirus, and vesicular stomatitis virus. Vaccinia virus (VV) has been used to express in mammalian cell lines, or deliver to animal models, various proteins of RSV (Olmstead et al., PNAS 83:7462-7466 (1986); Wertz et al., J. Virol 63:4767-4776 (1989)). Similarly, similar constructs with the altered cDNA for RSV G protein inserted into the thymidine kinase gene of VV may be utilized to synthesize the altered G protein or polypeptide. For example, the methods detailed by Ball et al., (Proc. Natl. Acad. Sci. USA 83:246-250 (1986)) or Olmstead et al., (Proc. Natl. Acad. Sci. USA 83:7462-7466 (1986)) can be used to express the altered G protein or the F protein/altered G protein chimera from vaccinia virus vectors. Similar procedures, or modifications thereof, can be employed to prepare recombinant proteins according to the present invention by microbial means or tissue-culture technology. Accordingly, the invention pertains to the production of altered G proteins or polypeptides by recombinant technology.

In addition to the foregoing host cell systems in which the altered G proteins or polypeptides of this invention are produced in vitro, a variety of systems are appropriate for expression and delivery of such altered G proteins and polypeptides in vivo. These systems utilize attenuated pathogens such as bacteria or viruses as delivery agents. These live attenuated pathogens have inserted within them as a heterologous nucleic acid segment the nucleic acid sequence encoding the desired altered G proteins or polypeptides of this invention. Using these systems, the desired altered G proteins or polypeptides are expressed by a live, attenuated bacterium or virus within the body of a vertebrate.

Examples of such live attenuated pathogens include, but are not limited to, the live attenuated bacteria such as Salmonella described in U.S. Pat. No. 4,837,151, which is particularly suitable for oral delivery.

Further examples of live attenuated pathogens include live, attenuated alphaviruses, including, but not limited to, Venezuelan Equine Encephalitis virus, Sindbis virus and Semliki Forest virus. The Venezuelan Equine Encephalitis virus described in U.S. Pat. No. 5,643,576 is particularly suitable for subcutaneous, intramuscular, intranasal or inhalation delivery.

Various aspects of the preparation and use of alphaviruses as vectors, including, but not limited to, the making of attenuating mutations, the preparation of replicon systems, the insertion of one or more heterologous nucleic acid sequences, the use of helper cells, the selection of promoters, and the administration of such alphaviruses, are described in U.S. Pat. Nos. 5,185,440, 5,505,947, 5,643,576, 5,792,462, 6,156,558, 6,521,235, 6,531,135, and 6,541,010, and Published International Application WO 02/18585.

Further examples of live attenuated pathogens include live, attenuated, non-segmented negative strand RNA viruses of the Order designated Mononegavirales. The nucleic acid molecule encoding the altered G polypeptide is inserted as a heterologous sequence into such a virus using the rescue (also known as reverse genetics) technique. Where the virus is RSV, the nucleic acid molecule encoding the altered G polypeptide replaces the native sequence encoding the complete G protein. When the virus is a Mononegavirales other than RSV, the nucleic acid molecule can replace coding sequence in the virus, can be fused to a portion of a glycoprotein coding sequence in the virus, or can be inserted as a supernumerary sequence in the virus in, for example, an intergenic region.

The basic rescue technique, including the insertion of a heterologous sequence, was described in U.S. Pat. No. 6,033, 886. Rescue has been described for various Mononegavirales, including, but not limited to, the following: RSV (U.S. Pat. No. 5,716,821), parainfluenza viruses, including PIV-3 (U.S. Pat. No. 6,248,578), PIV-1 (Published International Application WO 2003/043587), PIV-2 (Published International Application WO 2004/027037), measles virus (Published International Application WO 97/06270), mumps virus (Published International Application WO 01/09309), vesicular stomatitis virus (U.S. Pat. No. 6,168,943), and human metapneumovirus (U.S. Published Application 20040005544).

Techniques directed to improved rescue, such as heat shock and plaque expansion, are described in U.S. Pat. No. 6,673,572. Additional techniques directed to improved rescue, such as the transient expression of an RNA polymerase, such as T7, from a transiently transfected expression vector, electroporation, and calcium phosphate transfection, are described in International Application PCT/US04/18305, filed Jun. 8, 2004, which claims priority from U.S. Provisional Patent Application 60/477,389, filed Jun. 9, 2003.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also pertains to immunogenic compositions comprising altered G proteins and polypeptides described herein. For instance, an altered G polypeptide or protein, or product thereof, of the present invention can be formulated with a physiologically acceptable diluent or carrier to prepare an immunogenic composition. The particular physiological diluent or carrier may include, but is not limited to, sterile water, buffered saline, polyols (e.g., glycerol, propylene glycol, liquid polyethylene glycol) and dextrose solutions. The optimum concentration of the active ingredient(s) in the chosen vehicle can be determined empirically, according to well-known procedures, and will depend on the ultimate pharmaceutical formulation desired.

The altered G protein or polypeptide (or admixture, fusion protein or chimera thereof) can be used as an antigen to elicit an immune response to the antigen in a vertebrate, such as a mammalian host. For example, the antigen can be all or an immunogenic portion of the altered G protein or a chimera of the altered G protein or polypeptide and all or an immunogenic portion of the RSV F protein. The descriptions herein relating to compositions comprising an altered G protein or polypeptide are intended to include compositions comprising an altered G protein or polypeptide along with all or a portion of the RSV F protein.

The method of the present invention comprises administering to the vertebrate an immunologically effective dose of an immunogenic composition comprising a mixture of an altered G protein or polypeptide and any suitable adjuvant. As used herein, an "adjuvant" is intended to mean any agent that is sufficient to enhance or modify the immune response to the antigen. As used herein, an "immunologically effective" dose of the immunogenic composition is a dose that is suitable to elicit an immune response. The particular dosage will depend upon the age, weight and medical condition of the vertebrate to be treated, as well as on the method of administration. The skilled artisan will readily determine suitable doses. The immunogenic composition can be optionally administered in a pharmaceutically or physiologically acceptable vehicle, such as physiological saline or ethanol polyols such as glycerol or propylene glycol.

Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (see below) or bacterial cell wall components), such as, for example, (a) MF59 (PCT Publ. No. WO 90/14837), containing 5% Squalene, 0.5% Tween 80, and 0.5% Span 85 (optionally containing various amounts of MTP-PE (see below, although not required)) formulated into submicron particles using a microfluidizer such as Model 10% microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113, 918; one such AG P is 2-[(R)-3-Tetradecanoyloxytetradecanoylamino]ethyl 2-Deoxy-4-O-phosphono-3-O-[(R)-3-tetradecanoyloxytetradecanoyl]-2-[(R)-3-tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207, 646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an *E. coli* heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

As mentioned above, muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

The compositions of this invention can be administered to a human or animal by a variety of routes, including parenteral, intrarterial, intradermal, transdermal (such as by the use of slow release polymers), intramuscular, intraperitoneal, intravenous, subcutaneous, oral and intranasal routes of administration. The amount of altered G protein employed in such compositions will vary depending upon the route of administration and physical characteristics of the subject vertebrate. Adjustment and manipulation of established dosage ranges used with traditional carrier antigens for adaptation to the present composition is well within the ability of those skilled in the art. The compositions of the present invention are intended for use in the treatment of both immature and adult vertebrates, and, in particular, humans.

The altered G protein can be administered in conjunction with additional immunogens, including all or a portion of RSV F protein; the altered G protein or polypeptide can be administered separately, sequentially or concurrently with the additional immunogen. For example, the altered G protein or polypeptide can be given in an admixture with all or a portion of RSV F protein.

The altered G protein or polypeptide of the present invention can be coupled to a carrier molecule in order to modulate or enhance the immune response. Suitable carrier proteins include bacterial toxins that are safe for administration to vertebrates and immunologically effective as carriers. Examples include pertussis, diphtheria, and tetanus toxoids and non-toxic mutant proteins (cross-reacting materials (CRM)), such as the non-toxic variant of diphtheria toxoid, $CRM_{197}$. Fragments of the native toxins or toxoids, which contain at least one T-cell epitope, are also useful as carriers for antigens. Methods for preparing conjugates of antigens and carrier molecules are well-known in the art and can be found, for example, in Wong, Chemistry of Protein Conjugation (CRC Press Inc., Ann Arbor, Mich. (1991)); Bernatowicz and Matsueda, Analytical Biochemistry 155:95-102 (1986); Frisch et al., Bioconjugate Chem. 7:180-186 (1996); and Boeckler et al., J. Immunological Methods 191:1-10 (1996).

In addition, if a particular peptide region (e.g., amino acids 151-221, amino acids 178-219) is deleted, one or more epitopes from an antigen from another organism, including, but not limited to, parainfluenza virus type 3, can be inserted into the deleted region, in order to create a bivalent immunogenic composition.

The invention also relates to an immunogenic composition comprising a physiologically acceptable diluent or carrier and a nucleic acid molecule encoding an altered G protein or polypeptide of RSV, wherein said altered G protein or polypeptide retains immunogenicity and, when incorporated into the immunogenic composition and administered to a vertebrate, does not induce enhanced disease upon subsequent infection of the vertebrate with RSV. Such a composition is referred to herein as a nucleic acid immunogenic composition or DNA immunogenic composition and is useful for the genetic immunization of vertebrates.

The term, "genetic immunization", as used herein, refers to inoculation of a vertebrate, particularly a mammal, with a nucleic acid immunogenic composition directed against a pathogenic agent, particularly RSV, resulting in the generation of an immune response by the vertebrate against RSV. A "nucleic acid immunogenic composition" or "DNA immunogenic composition" as used herein, is a nucleic acid construct comprising a nucleic acid molecule encoding a polypeptide antigen, particularly an altered G protein or polypeptide of RSV described herein. The nucleic acid construct can also include transcriptional promoter elements, enhancer elements, splicing signals, termination and polyadenylation signals, and other nucleic acid sequences. The nucleic acid immunogenic composition does not induce enhanced disease upon subsequent infection of the vertebrate with RSV.

The nucleic acid immunogenic composition is produced by standard methods. For example, using known methods, a nucleic acid (e.g., DNA) encoding an altered G protein or polypeptide of RSV, can be inserted into an expression vector to construct a nucleic acid immunogenic composition (see Maniatis et al., Molecular Cloning, A Laboratory Manual, 2nd edition, Cold Spring Harbor Laboratory Press (1989)).

The individual vertebrate is immunized with the nucleic acid immunogenic composition (i.e., the composition is administered), using standard methods. The vertebrate is immunized subcutaneously, intravenously, intraperitoneally, intradermally, intramuscularly, topically, orally, rectally, nasally, buccally, vaginally, by inhalation spray, or via an implanted reservoir in dosage formulations containing conventional non-toxic, physiologically acceptable carriers or vehicles. Alternatively, the vertebrate is inoculated with the nucleic acid immunogenic composition through the use of a particle acceleration instrument (a "gene gun"). The form in which it is administered (e.g., capsule, tablet, solution, emulsion) will depend in part on the route by which it is administered. For example, for mucosal administration, nose drops, inhalants or suppositories can be used.

The nucleic acid immunogenic composition can be administered in conjunction with any suitable adjuvant as described above. The adjuvant is administered in a sufficient amount, which is that amount that is sufficient to generate an enhanced immune response to the nucleic acid immunogenic composition. The adjuvant can be administered prior to, concurrently with, contemporaneously (simultaneously) with, or after inoculation with the nucleic acid immunogenic composition. The adjuvant can also be administered at more than one time. The adjuvant and the nucleic acid immunogenic composition can be administered at approximately the same location on the vertebrate; for example, both the adjuvant and the nucleic acid immunogenic composition are administered at a marked site on a limb of the vertebrate.

In a particular embodiment, the nucleic acid construct is co-administered with a transfection-facilitating agent. In one embodiment, the transfection-facilitating agent is dioctylglycylspermine (DOGS) (published PCT application publication no. WO96/21356). In another embodiment, the transfection-facilitating agent is bupivicaine (U.S. Pat. No. 5,593,972).

The invention also provides a method of immunizing a vertebrate, e.g., an RSV seronegative human, against RSV, comprising administering to the vertebrate a composition comprising an immunologically effective amount of altered G protein or polypeptide of RSV which retains immunogenicity and which, when incorporated into an immunogenic composition and administered to a vertebrate, does not induce enhanced disease upon subsequent infection of the vertebrate with RSV. Alternatively, the composition comprises a nucleic acid molecule encoding an immunologically effective amount of altered G protein or polypeptide of RSV which retains immunogenicity and which, when incorporated into an immunogenic composition and administered to a vertebrate, does not induce enhanced disease upon subsequent infection of the vertebrate with RSV.

The teachings of all references cited herein are hereby incorporated herein by reference.

The following Examples are offered for the purpose of illustrating the present invention and are not to be construed as limiting the scope of this invention.

EXAMPLES

Materials and Methods

Cells and viruses. A549 (American Type Culture Collection [(ATCC CCL-185) Manassas, Va.], HEp-2 (ATCC CCL-23), and Vero (ATCC CCL-81) cells were maintained in culture as previously described (40). The viruses used in the present studies were wild-type RSV A2 (41), cp-RSV (42, 43), cpts 248/404 (44), rA2 cpts248/404ΔSH (45), and rA2cpΔG213 (40).

Plasmid construction. The recombinant RSV strains, rA2cpΔ50-222 and rA2cpΔ77-220, were made using previously-described reverse genetics techniques (40). In summary, the RSV genome from the cpts248/404 strain (44) (samples of this strain were previously deposited with ATCC and were assigned Accession Number VR-2454) was PCR-amplified in three large fragments designated Le-P, M-M2, and L (FIG. 1), followed by ligation into plasmids. To remove the portion of the genome encoding amino acids 151-221 or 178-219 of G protein, two DNA primers complementary to genomic sequences immediately flanking the nucleotides to be deleted were used to amplify the M-M2 plasmid (FIG. 1).

The sequence of the forward primer for the deletion of the portion encoding amino acids 151-221 is as follows:

(SEQ ID NO:5)
CGGGTACCAAGGTCTCATAGTTTGGCGTTGTTTTGTGGTGGGCTTGCTG

The sequence of the reverse primer for the deletion of the portion encoding amino acids 151-221 is as follows:

(SEQ ID NO:6)
CGGGTACCAAGGTCTCAACTAAATCAAAGGAAGTACCCACCACCAAGCC

The sequence of the forward primer for the deletion of the portion encoding amino acids 178-219 is as follows:

(SEQ ID NO:7)
CGGGTACCAAGGTCTCATAGTGCATATGCTGCAGGGTACAAAGTTGAACA
C

The sequence of the reverse primer for the deletion of the portion encoding amino acids 178-219 is as follows:

(SEQ ID NO:8)
CGGGTACCAAGGTCTCAACTAAATCAAAGGAAGTACCCACCACCAAGCC

Each of these primers contained a Bsa I restriction site (underlined). Extension from these primers on the M-M2 plasmid occurred in opposite directions such that the region of the G gene to be deleted was excluded from PCR amplification. Circularization of the PCR product occurred following digestion with Bsa I. The inserts from the modified M-M2 plasmid were digested with the restriction enzymes Aat II and Bam HI and ligated into the previously generated cDNA clone to cp-RSV (40). This approach resulted in a vector containing antigenomic cDNA having the full complement of RSV genes based upon cp-RSV and with specific deletions in G gene as desired (FIG. 1). This vector was used to transfect Vero cells and rescue infectious rRSV strains using techniques previously described (40). In summary, Vero cells (approximately $3 \times 10^5$ per T 12.5 $cm^2$ flask) were grown overnight to 50% confluence and transfected by calcium phosphate precipitation with the vector described above containing the full complement of RSV genes based upon cp-RSV and with specific deletions in G gene as desired (5 μg), and plasmids encoding the RSV support proteins N (400 ng), P (300 ng), L (200 ng) and M2 (200 ng), and T7 RNA polymerase (5 μg). Following a three hour incubation (at 32° C., 3% $CO_2$), the Vero cells were exposed to 44° C. for three hours, and then returned to 32° C., 3% $CO_2$. The monolayers were washed with HEPES-buffered saline, and the growth medium was replaced 24 hours post-transfection. Thereafter, the cells were cultured for two days (at 32° C., 5% $CO_2$), passed onto 50% confluent Vero cell monolayers in T 25 $cm^2$ flasks, and maintained (at 32° C., 5% $CO_2$) in DMEM containing HEPES, and supplemented with 10% FBS, 2 mM L-glutamine, 0.1 mM minimal essential medium non-essential amino acids, and 0.1% gentamicin (Invitrogen) for five additional days. The medium and cells were then harvested and stored at −80° C. The harvested cell lysate (600 μl) was diluted in 2 ml of DMEM and used to infect 50% confluent monolayers of Vero cells in T 25 $cm^2$ flasks. Following gentle rocking at room temperature for 1.5 hours, the monolayers were washed with phosphate-buffered saline (PBS) (Invitrogen), cultured in DMEM, and observed daily for syncytium formation. Typically, the cells were harvested onto 4 ml of growth medium and stored at −80° C. on day 7. The viruses were terminally diluted once, further amplified in Vero cells, snap frozen, and stored at −80° C.

Recombinant RSV (RSV). Recombinant RSV strains were purified from Vero cells over discontinuous sorbitol density gradients from cultures grown in complete DMEM (Dulbecco's Minimum Essential Media, Gibco BRL, Grand Island, N.Y.) supplemented with 5% FBS (Hyclone, Logan, Utah), 2 mM L-glutamine (Gibco BRL), and 2% Pen-strep (Gibco BRL). In brief, supernatants were harvested when the cytopathic effect was at least 75% and centrifuged at low speed (200 g, 15 minutes, 4° C.) to remove cellular debris. The clarified supernatant was added to a 50% PEG-NTE mixture (50% polyethylene glycol, 0.15M NaCl, 0.05M Tris, 1 nM EDTA) to yield a final concentration of 10% (V/V) PEG-NTE to supernatant. After stirring two hours (4° C.), the precipitate was pelleted (8,500 rpm, 30 minutes, 4° C.) using a Sorvall RC-5B Superspeed centrifuge with a GSA Rotor. The resulting pellet was resuspended in 20% (W/V) sorbitol-NTE Buffer and placed over the discontinuous sorbitol gradient. Purified virus was collected at the interface between 60% and 35% sorbitol-NTE and stored at −70° C.

Genome sequence confirmation. The consensus genome sequences of rescued viruses were confirmed by direct sequence analysis of RT/PCR products spanning the entire genome as previously described (40). Briefly, total RNA was extracted from amplified cell lysates using Trizol LS Reagent (Invitrogen, Carlsbad, Calif.) and used (1 μg) in the Prostar High Fidelity Single-Tube RT-PCR System (Stratagene, La Jolla, Calif.). The primer pairs were designed to amplify viral genome in seven fragments of approximately 2 kb each. Control reactions that did not undergo reverse transcription and negative control reactions with dH$_2$O substituted for RNA template were set up for each fragment. Amplification was performed in the GeneAmp 9700 (Applied Biosystems, Foster City, Calif.) and conditions were 48° C. for 45 minutes, 95° C. for 1 minute, 40 cycles of 30 seconds at 94° C., 30 seconds at 58° C., 6 minutes at 68° C., completed by a final extension step of 68° C. for 7 minutes. The amplified fragments were purified using the QIAquick PCR purification kit (Qiagen, Valencia, Calif.) and cycle sequencing was performed on 50-100 ng of purified fragment using the Big Dye Terminator v3.0 Ready Reaction Cycle Sequencing Kit (Applied Biosystems). Unincorporated dyes were removed using the DyeEx-96 kit (Qiagen) and automated sequence analysis was carried out on the 3100 Genetic Analyser (Applied Biosystems). Sequence data were aligned using Sequencher v4.0.5 (Gene Codes, Ann Arbor, Mich.).

Immunoblot. The protein concentrations of sorbitol density gradient purified rA2cpΔG150-222, rA2cpΔG177-220, cp-RSV, or wild-type A2 RSV were determined by BCA (Pierce, Rockford, Ill.) according to the manufacturer's instructions. Thereafter 5.0 µg virus protein was admixed with Laemmli sample buffer (Bio-Rad Laboratories; Hercules, Calif.) containing 5% (V/V) β-mercaptoethanol (Sigma; St. Louis, Mo.), subjected to electrophoresis in SDS 12% polyacrylamide (Bio-Rad Laboratories) gels, and transferred to nitrocellulose membranes (Bio-Rad Laboratories) for Western analysis. The immunoblots were incubated with monoclonal antibodies previously identified (40, 46) to react with regions of G protein encompassed by amino acids 1-118 (131-2G), 174-193 (L9), and 215-298 (130-2G). K6-1 murine mAb directed against G protein was also used in the studies. Reactivity was visualized by secondary incubation with horseradish peroxidase conjugated to goat anti-mouse IgG (Kirkegaard and Perry Laboratories, Gaithersburg, Md.) followed by incubation with 4-chloro-napthol substrate (Sigma). Highly purified natural G protein (1 µg/lane) from the A2 strain of RSV served as control.

Quantitative PCR (qPCR). RSV genome copy number in infected A549 monolayers was determined as previously described by quantitative PCR (40) using a DNA primer-probe set (Synthegen, LLC, Houston, Tex.) specific for the L gene of RSV. In brief, the sequences of primers and probe were: RSVAF forward primer (5'-AGACAAGCTAAAAT-TACTAGCGAAATCA-3') (SEQ ID NO:9), RSVAP FAM/TAMRA probe (5'-TAGACTGGCAGTTACAGAGGTT-3') (SEQ ID NO:10), and RSVAR reverse primer (5'-GTTGTG-CACTTTTGGAGAATATTTTG-3') (SEQ ID NO:11). The sequences were 100% conserved for all strains in the study. PCR cycling conditions were 50° C. for 2 minutes, 95° C. for 10 minutes, 40 cycles at 95° C. for 15 seconds, and 60° C. for 1 minute. Equal loading was verified using a TaqMan® ribosomal RNA control reaction kit that amplified human 18S cDNA (Applied Biosystems). Variations between ribosomal RNA concentrations from each total cellular RNA isolation was in most instances less than 0.5%. PCR, fluorescence detection, and data analysis were performed on an ABI Prism 7700 Sequence Detector (Perkin-Elmer, Pittsburgh, Pa.).

Animal studies. Female BALB/c and C57Bl/6 mice (8-10 weeks of age) were obtained respectively from Charles River Laboratories (Wilmington, Mass.) and Jackson Laboratories (Bar Harbor, Me.) and housed in a facility accredited by the American Association for Accreditation of Laboratory Animal Care. Natural G glycoprotein was purified by immunoaffinity chromatography from Vero cells infected with the A2 strain of RSV (47). G protein was greater than 90% pure as estimated by SDS-PAGE and antigen-capture ELISA. Immunizations (1.0 µg per dose) with natural G protein prepared in PBS alone were intramuscular (0.1 ml). Additional control mice were injected with G protein admixed with CpG adjuvant (100 µg/dose, 5' GCATGA<u>C</u>GTTGAGCT 3') (SEQ ID NO:12) as previously described (27). Intranasal (0.05 ml) immunizations by experimental infection (~10$^6$ PFU) or challenge (~10$^6$ PFU) with the A2 strain of RSV were performed under sedation (ketamine and xylazine, The Butler Co., Dublin Ohio, 60 mg/kg). Eosinophilia was assessed 7 days after challenge as previously described (47) following bronchoalveolar lavage (BAL) and the examination of at least 400 leukocytes in cytospin-preparations of BAL fluids stained with Diff-Quik (Dade International, Miami, Fla.).

Plaque assays. Infectious virus titers in culture supernatants or lungs after experimental infection or challenge were determined by plaque assay using HEp-2 cell monolayers as previously described (14, 47). Sensitivity of mutant viruses to temperature was determined at 32, 37, 39, and 40° C. (40). Pulmonary tissues were collected 4 and 7 days after primary experimental infection, or in efficacy studies 4 days after challenge.

Serum antibody determinations. Endpoint ELISA and the plaque reduction neutralization test were used to respectively ascertain geometric mean serum anti-F protein IgG and neutralization titers (14, 47). The neutralization titers were determined against the A2 strain of RSV in the presence or absence of 5% (V/V) guinea pig serum (BioWhittaker, Walkersville, Md.) as a source of complement (C). The neutralization titers were calculated as the reciprocal of the serum dilution that showed 60% reduction (relative to the virus control) in the number of foci per well.

Statistical analyses. Significant differences ($p<0.05$) were determined after log transformation by Tukey-Kramer HSD multiple comparison or Student's t test using JMP® statistical discovery software (SAS Institute Inc., Cary, N.C.). The data are expressed ±1 standard deviation. All data were confirmed in separate studies.

Example 1

Construction of Recombinant RSV Strains with Altered G Protein

The recall responses of T cells from mice (15) and humans (16) against G protein appear to be directed primarily against epitopes within the ectodomain encompassed by amino acids 149 to 200. To diminish T cell responses to G protein and improve safety, anti-genomic cDNAs were constructed wherein nucleotides (nt) in this region were deleted (FIG. 1). From one cDNA, 123 nt (positions 5221 to 5344) encoding 41 amino acids (178 to 219) were deleted. The second cDNA was deleted of 210 nt (positions 5140 to 5350) that encoded 70 amino acids (151-221). The rRSV strains were rescued as previously reported (40) and respectively designated rA2cpΔG177-220 (SEQ ID NOS:3 and 4) and rA2cpΔG150-222 (SEQ ID NOS:1 and 2). The appropriate mutations for each rRSV strain were confirmed following consensus genomic sequencing of RT/PCR products spanning the entire genome. Additional alterations in the genome and gene for G protein were not detected (data not shown).

Figure 2:
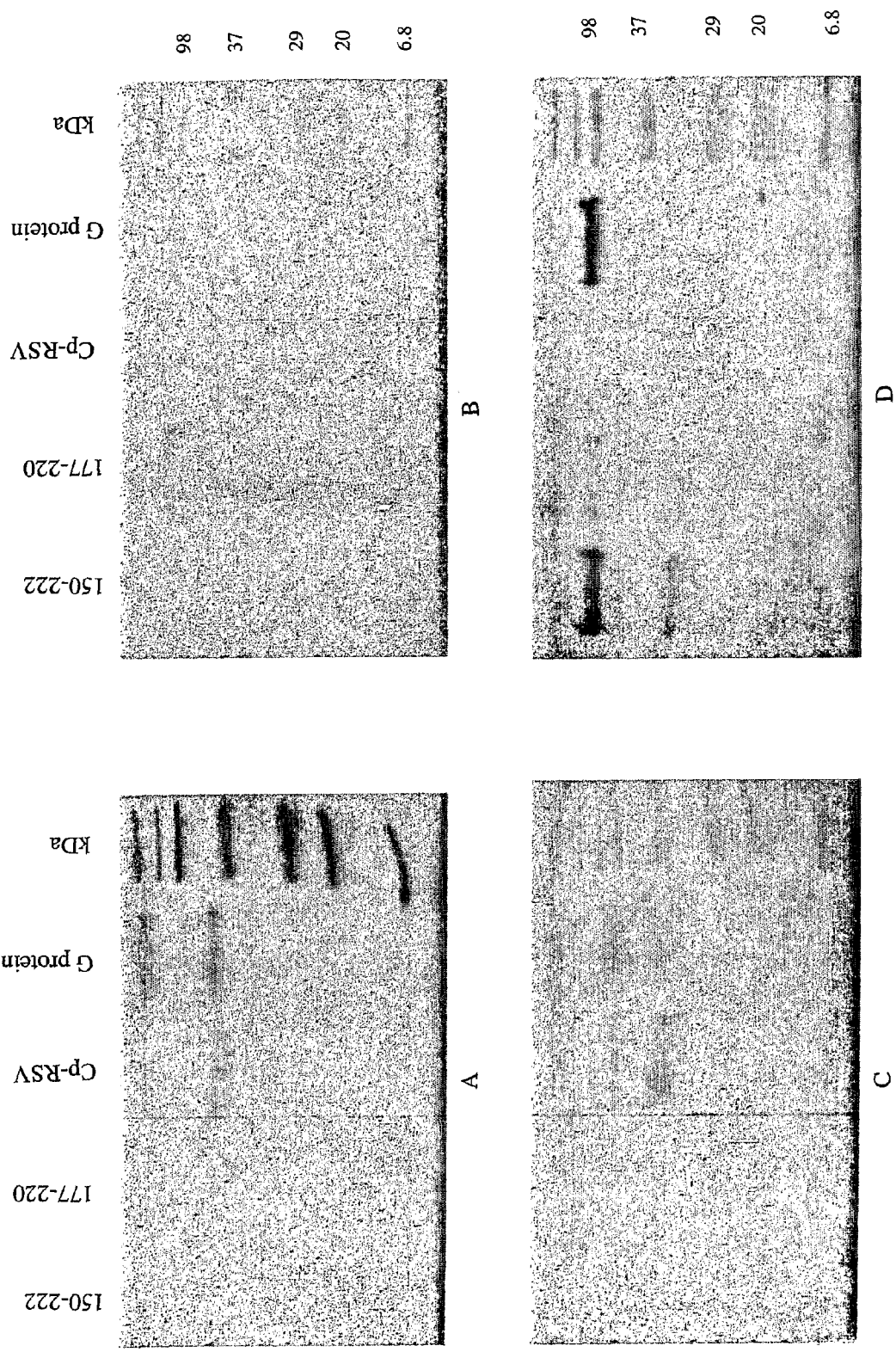
FIG. 2 depicts Western blot analysis of rRSV strains with altered G protein. Strains rA2cpΔG150-222, rA2cpΔG177-220, and cp-RSV were purified from Vero cells over discontinuous sorbitol density gradients and compared to native G protein by immunoblot using K6-1 mAb (B), or mAb that reacted with regions of G protein spanned by amino acids 1-118 (A), 174-193 (C), or 215-298 (D). Molecular weight markers are depicted on the right.

Further confirmation that the engineered deletions were correct was provided by immunoblotting of sorbitol density gradient purified rA2cpΔG177-220 and rA2cpΔG150-222 with monoclonal antibodies reported (40, 46) to react with specific regions of G protein. Both rA2 cpΔG177-220 and rA2cpΔG150-222 were visualized when probed with a monoclonal antibody (130-2G) that reacted with an epitope within the C terminal region spanned by amino acids 214-298 (FIG. 2D). As expected, the staining pattern also indicated that G protein of rA2cpΔG150-222 migrated farther during SDS-PAGE than that of rA2cpΔG177-220 or cp-RSV (FIG. 2D). As expected, when probed with a monoclonal antibody (L9) that binds the region encompassed by amino acids 174 to 193, G proteins from rA2cpΔG177-220 and rA2cpΔG150-222 were not visualized (FIG. 2C). Probing HEp-2 cell monolayers with 130-2G three days after infection with rA2cpΔG150-222 or rA2cpΔG177-220 resulted in positive staining (Table 1).

In contrast, plaques were not stained following with L9 monoclonal antibody (Table 1). Of interest were results obtained after probing with 131-2G monoclonal antibody (Table 1 and FIG. 2A). The HEp-2 cell monolayers did not react with 131-2G monoclonal antibody when infected with rA2cpΔG150-222 and G protein was not visualized on immunoblot. Thus, deletion of amino acids 151-221 appeared to affect a conformational epitope in the region spanned by amino acids 1-118. It was also noteworthy that construction of the rRSV strains enabled identification of the epitope recognized by the K6-1 mAb. The results in Table 1 and immunoblot depicted in FIG. 2B demonstrated that the epitope recognized by the K6-1 mAb is located in the region of G protein spanned by amino acids 150-174. As expected, G protein following infection with cp-RSV was visualized by all mAb (Table 1 and FIGS. 2 A-D). Plaques following infection with rA2cpΔG213, where G protein was genetically truncated at amino acid 213, were not positively stained with 130-2G mAb (Table 1).

Example 2

In Vitro Growth Characteristics of Recombinant RSV Strains Designated rA2cpΔG177-220 and rA2cpΔG150-222

Replication of the mutant viruses was characterized by qPCR and standard plaque assays using human lung epithelial cells (A549) cultured at 37° C. Table 2 shows results from a representative qPCR assay wherein temporal increases in RSV genome copy number following infection with rA2cpΔG177-220 or rA2cpΔG150-222 were contrasted with that of cp-RSV (parent virus), rA2cpΔG213 (40), wild-type A2, and temperature sensitive cpts248/404 (48) strains of RSV.

TABLE 1

Monoclonal antibody mapping of rA2cpΔG150-222 and rA2cpΔG177-220

| Virus[a] | Reactivity with mAb that bind regions spanned by amino acids[b]: | | | |
|---|---|---|---|---|
| | 1-118 (131-2G) | 1-298 (K6-1) | 174-193 (L9) | 214-298 (130-2G) |
| rA2cpΔG150-222 | Neg. | Neg. | Neg. | Pos. |
| rA2cpΔG177-220 | Pos. | Pos. | Neg. | Pos. |
| rA2cpΔG213 | Pos. | Pos. | Pos. | Neg. |
| cp-RSV | Pos. | Pos. | Pos. | Pos. |

[a]HEp-2 cell monolayers were infected with the denoted virus. Three days thereafter, the monolayers were probed with the indicated anti-G protein mAb.
[b]The following mAb were used to confirm genetic alterations of G protein: 131-2G (1-118), K6-1 (1-298), L9 (174-193), and 130-2G (214-298). Neg. and Pos. respectively denote negative and positive staining of recombinant RSV strains infecting HEp-2 cell monolayers.

TABLE 2

The replication of rRSV strains with genetically altered G protein in A549 lung epithelial cells

| | Hours post infection | | | | | | | | |
|---|---|---|---|---|---|---|---|---|---|
| | 24 h | | | 48 h | | | 72 h | | |
| Group[a] | Copy #[b] | FoldΔ[c] | PFU[d] | Copy #[b] | FoldΔ[c] | PFU[d] | Copy #[b] | FoldΔ[c] | PFU[d] |
| rA2cpΔG150-222 | 14.2 | 1.2 | 23.0 | 46.1 | 2.0 | 40.5 | 70.0 | 2.1 | 115.0 |
| rA2cpΔG177-220 | 12.6 | 1.3 | 4.3 | 35.6 | 2.6 | 34.0 | 47.2 | 4.0 | 95.0 |
| rA2cpΔG213 | 3.2 | 5.1 | 0.005 | 12.4 | 7.3 | 0.2 | 17.3 | 11.0 | 2.3 |
| A2 | 23.0 | 0.7 | 25.0 | 101.9 | 0.9 | 360.0 | 183.5 | 1.0 | 2,700.0 |
| cp-RSV | 16.5 | — | 22.5 | 90.63 | — | 315.0 | 189.4 | — | 3,300.0 |
| cpts248/404 | 0.3 | 66.0 | ND | 0.9 | 103.0 | 0.1 | 1.5 | 123.0 | 0.9 |
| Control | ND[e] | — | ND | ND | — | ND | ND | — | ND |

[a]A549 cells were infected (moi = 0.09) with the indicated virus.
[b]Copy # denotes genome copy number X$10^3$.
[c]FoldΔ denotes difference in genome copy relative to cp-RSV.
[d]PFU is plaque-forming units X$10^3$ of indicated virus per ml culture medium.
[e]ND denotes not detected.

The results indicated the rate of genome synthesis 24 hours after infection with rA2cpΔG177-220 or rA2cpΔG150-222 was slightly less than that of parent (cp-RSV) or RSV A2. After 72 hours, genome copy numbers of the recombinant RSV strains were approximately 47,000 and 70,000 respectively, and approximately 2 and 4 fold less when compared to nearly 190,000 copies detected in A549 monolayers infected with cp-RSV. In comparison, only 17,300 (11 fold decrease) and 1,500 (123 fold decrease) copies of attenuated rA2cpΔG213 (40) and temperature sensitive cpts248/404 genomes were respectively detected by qPCR.

To characterize replication of rA2cpΔG177-220 and rA2cpΔG150-222 further, standard plaque assays were used to detect infectious virus in the culture supernatants (Table 2). The infectious virus titers recovered from A549 cells infected with rA2cpΔG177-220 or rA2 cpΔG150-222 were similar to cp-RSV 24 hours post infection. However, 48 and 72 hours post infection the titers were approximately 10 fold less relative to cp-RSV and A2 strains of RSV. As previously described, replication of rA2cpΔG213 (40) and cpts248/404 (48) strains were significantly restricted in vitro. Infectious virus titers were 1,000 fold less than that of cp-RSV or A2 strains of RSV (Table 2). Thus, replication of rA2cpΔG177-220 and rA2cpΔG150-222 in A549 cells at 37° C. was less than that of the parent virus, but not restricted to the level of rA2cpΔG213 and cpts248/404.

Figure 3:
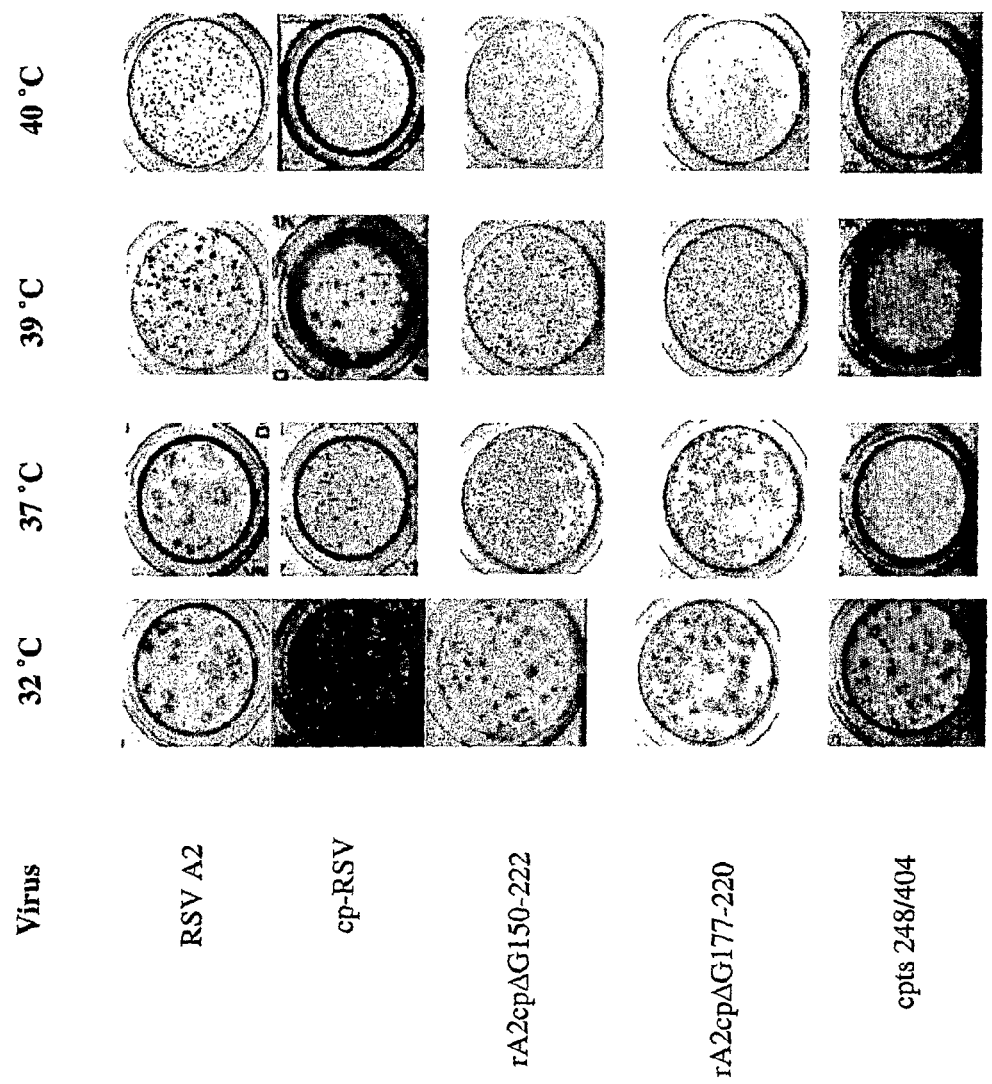
FIG. 3 depicts plaque morphology of rRSV strains with altered G protein. A549 monolayers were infected with the indicated virus and cultured for 3-4 days at the denoted temperature. The plaques were visualized by immunostaining with mAb reactive with F protein.

Next ascertained was the sensitivity of rA2cpΔG177-220 and rA2cpΔG150-222 to temperature. HEp-2 cell monolayers were infected and after 3 to 5 days culture at 32, 37, 39, or 40° C., plaques were visualized by immunostaining for F protein (FIG. 3). When plaque morphology from cultures infected with rA2cpΔG177-220 or rA2cpΔG150-222 were compared with cp-RSV, few differences were noted. Indeed, pinpoint plaques were readily observed at 39° C. In monolayers infected with cpts248/404, plaques were observed at 32° C., but not 37° C., in agreement with the previously reported (48) shut-off temperature. Thus, deletion of amino acids 151 to 221 did not confer biologically relevant sensitivity to temperature.

Example 3

Immunogenicity and Efficacy of Recombinant RSV Immunogenic Compositions

Figure 4:
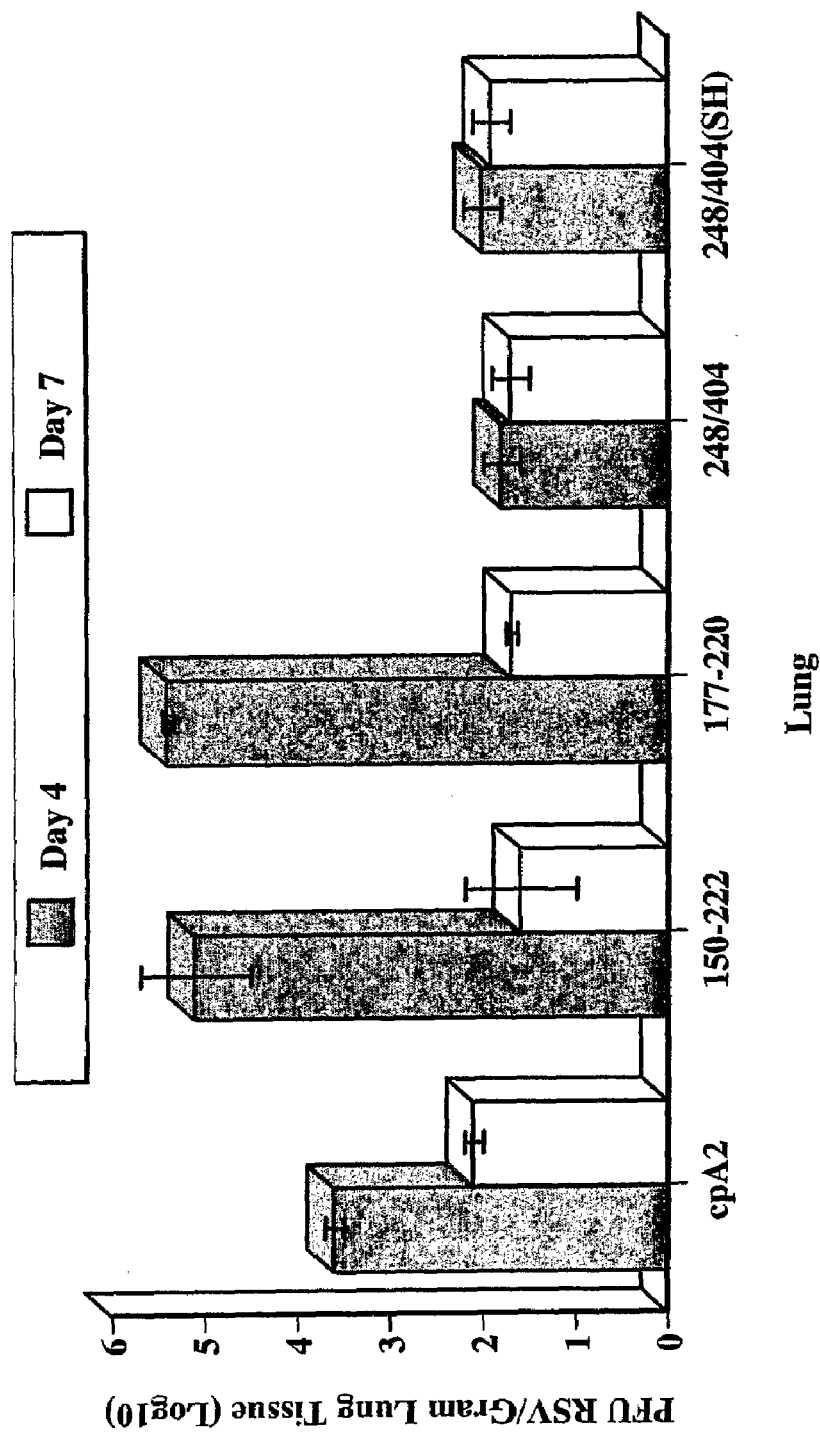
FIG. 4 depicts the replication of rRSV strains in the respiratory tract of BALB/c mice. Naive BALB/c mice were infected (∼1×10$^6$ PFU) with the indicated viruses. Lung tissues were collected four and seven days thereafter for the determination of infectious virus titer (±.1 standard deviation) by plaque assay. There were five mice per group.
Figure 5:
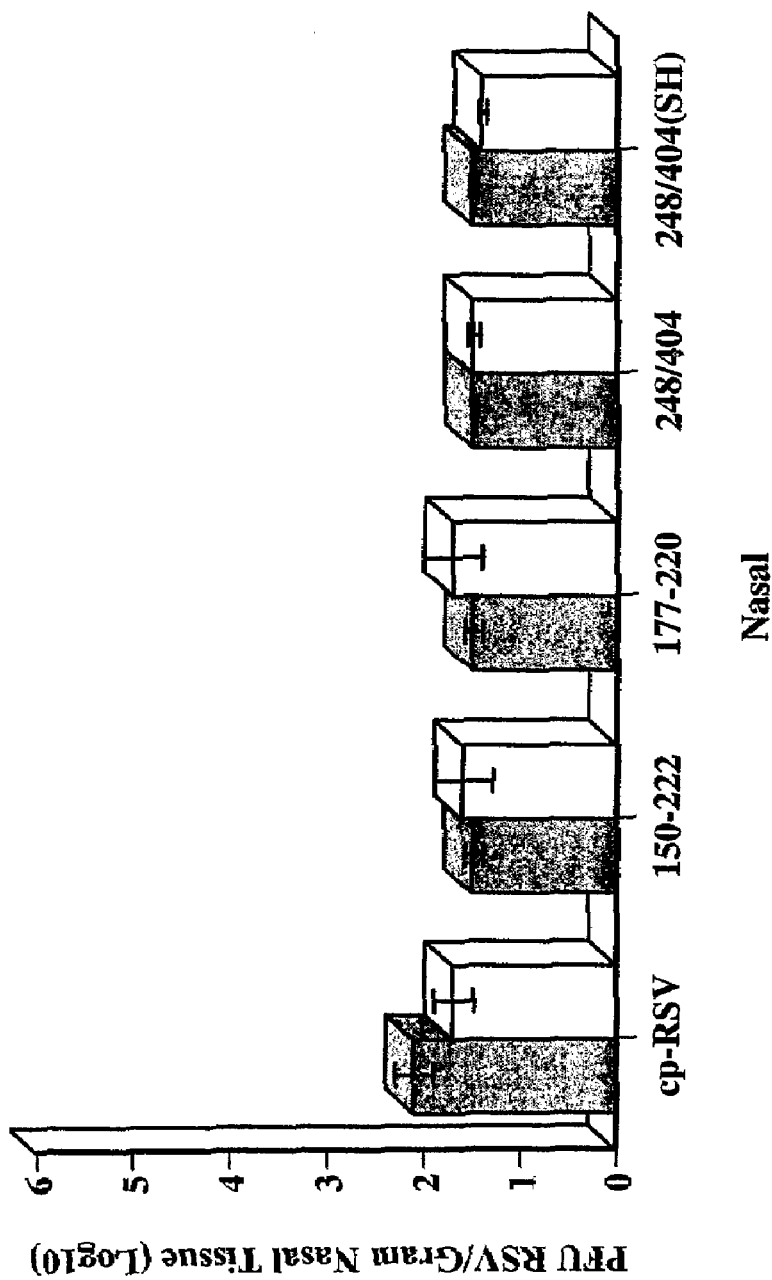
FIG. 5 depicts the replication of rRSV strains in the respiratory tract of BALB/c mice. Naive BALB/c mice were infected (∼1×10$^6$ PFU) with the indicated viruses. Nasal tissues were collected four and seven days thereafter for the determination of infectious virus titer (±.1 standard deviation) by plaque assay. There were five mice per group.

The capacity of the genetically altered viruses to replicate in the respiratory tract was examined after experimental infection of BALB/c mice. The results indicated that deletion of amino acids 151 to 221 did not lead to restricted replication in vivo. The virus titers in lungs (FIG. 4) and nasal (FIG. 5) tissues four days after infection with rA2cpΔG177-220 or rA2cpΔG150-222 were not significantly less than that of the parent virus. As previously reported (49, 48), replication of cpts248/404 and rA2 cpts248/404ΔSH viruses was severely limited in vivo. Because G protein is a major protective antigen, several studies were also performed to ascertain the capacity of rA2cpΔG177-220 or rA2cpΔG150-222 to induce efficacious immune responses in BALB/c mice. Four weeks after primary infection with rA2cpΔG177-220 or rA2 cpΔG150-222, noteworthy serum complement-assisted neutralization titers were observed (Table 3).

TABLE 3

The immune responses of BALB/c mice immunized with rA2cpΔ150-222 or rA2cpΔG177-220

| | | Antibody Titers ($\log_{10}$)[a] | | |
|---|---|---|---|---|
| | | F protein | Neutralizing | |
| Virus | PFU RSV[b] | IgG | +C | −C |
| cp-RSV | <1.7 ± 0.03 | 4.6 ± 0.4 | 1.5 ± 0.1 | <1.0 |
| rA2cpΔG150-222 | <1.7 ± 0.04 | 5.3 ± 0.4[d] | 2.2 ± 0.4[d] | <1.3 ± 0.2 |
| rA2cpΔG177-220 | <1.7 ± 0.03 | 5.2 ± 0.4[d] | 2.1 ± 0.6[d] | <1.0 |
| cpts248/404 | 2.0 ± 0.7 | 3.8 ± 0.2 | 1.3 ± 0.3 | <1.0 |
| rA2cpts248/404ΔSH | <1.7 ± 0.1 | 4.0 ± 0.2 | 1.3 ± 0.1 | <1.0 |
| PBS | 5.6 ± 0.04[c] | <1.7 | <1.0 | <1.0 |

[a] The titers are geometric means (±1 standard deviation) derived from serum samples collected 4 weeks after primary experimental infection. Neutralization titers were ascertained in the presence (+) or absence (−) of 5% serum as a source of complement (C). There were 5 mice per group.
[b] The numbers are geometric mean (±1 standard deviation) plaque forming units ($\log_{10}$) per gram of tissue 4 days after challenge with the A2 strain of RSV. There were 5 mice per group.
[c] $p < 0.05$ vs. all.
[d] $p < 0.05$ vs. cpts248/404 and rA2cpts248/404ΔSH.

The titers were comparable to those elicited following infection with cp-RSV virus and significantly greater than titers generated after infection with temperature sensitive cpts248/404 or rA2 cpts248/404ΔSH strains. Genetic alteration of G protein did not affect the induction of anti-F protein IgG titers. They were also significantly greater than titers generated after infection with temperature sensitive strains and comparable to parent virus (Table 3). Most importantly, the immune responses induced following infection were efficacious. Four days after challenge with the A2 strain of RSV a 3.9 $\log_{10}$ reduction in infectious virus titer was observed in the lungs compared with naïve mice.

Figure 6:
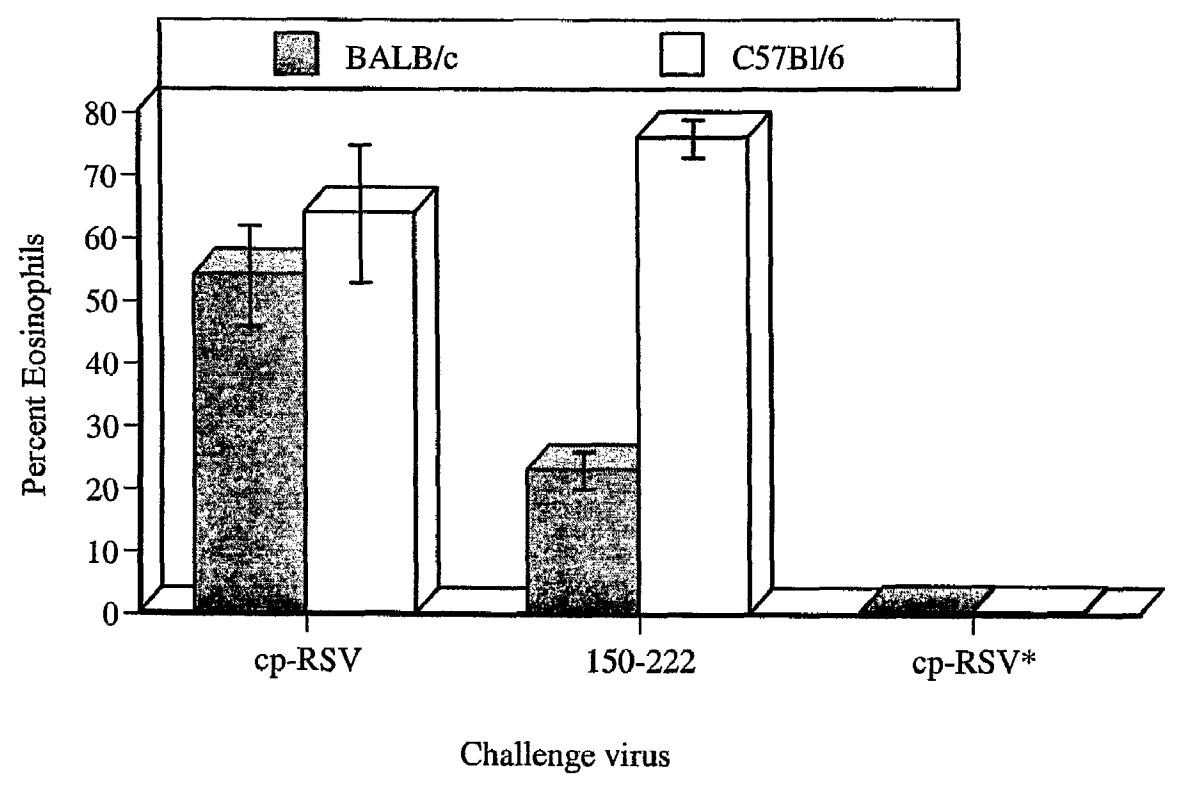
Figure 7:
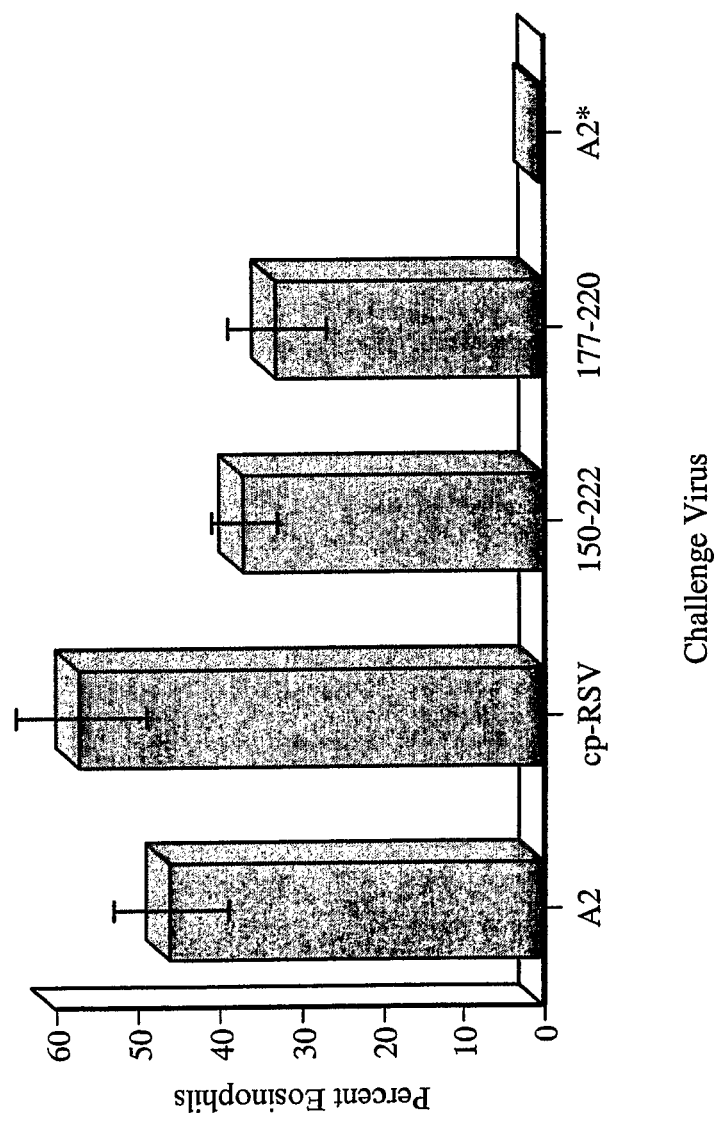
FIG. 7 depicts eosinophilia in the lungs of native G protein sensitized mice after challenge with rRSV. BALB/c (H2$^d$) and C57Bl/6 (H2$^b$) mice were injected intramuscularly on weeks 0 and 2 with native G protein (1.μg/dose) prepared in PBS alone. The mice were challenged with the indicated virus two weeks after the last injection and pulmonary eosinophilia (±.1 standard deviation) was assessed seven days thereafter. Eosinophilia was significantly (p<0.05) reduced in BALB/c mice challenged with the rRSV. The asterisk denotes control mice immunized with native G protein admixed with CpG oligonucleotide adjuvant (100.μg/dose) and challenged with A2 strain of RSV. There were five mice per group.

Next estimated was the potential of rA2 cpΔG177-220 or rA2 cpΔG150-222 to induce type 2 T cell responses and pulmonary eosinophilia. To accomplish this, polarized type 2 T cell responses were first induced in naïve BALB/c mice following immunization with native G protein prepared in PBS. Control mice were immunized with native G protein admixed with a CpG oligonucleotide adjuvant previously shown to increase type 1 T cell responses (27). Thereafter the capacity of the recombinant RSV strain to recall type 2 T cell responses after challenge was determined. FIG. 6 depicts pulmonary eosinophilia in mice primed with native G protein and challenged two weeks thereafter with rA2cpΔG150-222 or cp-RSV. The data demonstrated that eosinophilia was significantly reduced (from 54±8% to 23±3%) in the lungs of BALB/c mice relative to cp-RSV. Similar results were observed in mice immunized on weeks 0 and 2 with native G protein and challenged with rRSV strains with altered G protein (FIG. 7). As expected, pulmonary eosinophilia was not observed after challenge of mice immunized with G/CpG. Thus, genetic elimination of amino acids 151-221 or 178-219 removed epitopes important in the generation of T cell responses that lead to pulmonary eosinophilia in BALB/c mice. Pulmonary eosinophilia was not affected in C57Bl/6 mice primed with G protein and challenged with rA2cpΔG150-222.

REFERENCES

1. Collins, P. L., Y. T. Huang, and G. W. Wertz. 1984. Identification of a tenth mRNA of respiratory syncytial virus and assignment of polypeptides to the 10 viral genes. J. Virol. 49:572-8.

2. Huang, Y. T., and G. W. Wertz. 1983. Respiratory syncytial virus mRNA coding assignments. J. Virol. 46:667-72.
3. Kneyber, M. C., and J. L. Kimpen. 2002. Current concepts on active immunization against respiratory syncytial virus for infants and young children. Pediatr. Infect. Dis. J. 21:685-96.
4. Piedra, P. A. 2003. Clinical experience with respiratory syncytial virus vaccines. Pediatr. Infect. Dis. J. 22:S94-9.
5. Murphy, B. R., and P. L. Collins. 2002. Live-attenuated virus vaccines for respiratory syncytial and parainfluenza viruses: applications of reverse genetics. J Clin Invest 110: 21-7.
6. Martinez, F. D. 2003. Respiratory syncytial virus bronchiolitis and the pathogenesis of childhood asthma. Pediatr. Infect. Dis. J. 22:S76-82.
7. Sigurs, N. 2002. A cohort of children hospitalised with acute RSV bronchiolitis: impact on later respiratory disease. Paediatr. Respir. Rev. 3:177-83.
8. Bui, R. H., G. A. Molinaro, J. D. Kettering, D. C. Heiner, D. T. Imagawa, and J. W. St Geme, Jr. 1987. Virus-specific IgE and IgG4 antibodies in serum of children infected with respiratory syncytial virus. J. Pediatr. 110:87-90.
9. Jackson, M., and R. Scott. 1996. Different patterns of cytokine induction in cultures of respiratory syncytial (RS) virus-specific human TH cell lines following stimulation with RS virus and RS virus proteins. J. Med. Virol. 49:161-9.
10. Rabatic, S., A. Gagro, R. Lokar-Kolbas, V. Krsulovic-Hresic, Z. Vrtar, T. Popow-Kraupp, V. Drazenovic, and G. Mlinaric-Galinovic. 1997. Increase in CD23+ B cells in infants with bronchiolitis is accompanied by appearance of IgE and IgG4 antibodies specific for respiratory syncytial virus. J. Infect. Dis. 175:32-7.
11. Larche, M., D. S. Robinson, and A. B. Kay. 2003. The role of T lymphocytes in the pathogenesis of asthma. J. Allergy Clin. Immunol. 111:450-463.
12. Graham, B. S., T. R. Johnson, and R. S. Peebles. 2000. Immune-mediated disease pathogenesis in respiratory syncytial virus infection. Immunopharmacology 48:237-247.
13. Openshaw, P. J., S. L. Clarke, and F. M. Record. 1992. Pulmonary eosinophilic response to respiratory syncytial virus infection in mice sensitized to the major surface glycoprotein G. Int. Immunol. 4:493-500.
14. Hancock, G. E., D. J. Speelman, P. J. Frenchick, M. M. Mineo-Kuhn, R. B. Baggs, and D. J. Hahn. 1995. Formulation of the purified fusion protein of respiratory syncytial virus with the saponin QS-21 induces protective immune responses in Balb/c mice that are similar to those generated by experimental infection. Vaccine 13:391-400.
15. Hancock, G. E., P. W. Tebbey, C. A. Scheuer, K. S. Pryharski, K. M. Heers, and N. A. LaPierre. 2003. Immune responses to the nonglycosylated ectodomain of respiratory syncytial virus attachment glycoprotein mediate pulmonary eosinophilia in inbred strains of mice with different MHC haplotypes. J. Med. Virol. 70:301-8.
16. Hancock, G. E., C. A. Scheuer, R. Sierzega, K. S. Pryharski, J. T. McBride, L. F. Watelet, P. W. Tebbey, and J. D. Smith. 2001. Adaptive immune responses of patients with asthma to the attachment (G) glycoprotein of respiratory synctial virus. J. Infect. Dis. 184:1589-93.
17. Davies, D. E., J. Wicks, R. M. Powell, S. M. Puddicombe, and S. T. Holgate. 2003. Airway remodeling in asthma: New insights. J. Allergy Clin. Immunol. 111:215-225.
18. Fuhlbrigge, A. L., R. J. Adams, T. W. Guilbert, E. Grant, P. Lozano, S. L. Janson, F. Martinez, K. B. Weiss, and S. T. Weiss. 2002. The Burden of Asthma in the United States: Level and Distribution Are Dependent on Interpretation of the National Asthma Education and Prevention Program Guidelines. Am. J. Respir. Crit. Care Med. 166:1044-1049.
19. Hull, J., A. Thomson, and D. Kwiatkowski. 2000. Association of respiratory syncytial virus bronchiolitis with the interleukin 8 gene region in UK families. Thorax 55:1023-1027.
20. Lemanske, R. F. 2002. The Childhood Origins of Asthma (COAST) study. Pediatr Allergy Immunol 13:38-43.
21. Shay, D. K., R. C. Holman, R. D. Newman, L. L. Liu, J. W. Stout, and L. J. Anderson. 1999. Bronchiolitis-associated hospitalizations among US children, 1980-1996. JAMA 282:1440-6.
22. Anderson, L. J., P. Bingham, and J. C. Hierholzer. 1988. Neutralization of respiratory syncytial virus by individual and mixtures of F and G protein monoclonal antibodies. J. Virol. 62:4232-8.
23. Hancock, G. E., J. D. Smith, and K. M. Heers. 2000. Serum neutralizing antibody titers of seropositive chimpanzees immunized with vaccines coformulated with natural fusion and attachment proteins of respiratory syncytial virus. J. Infect. Dis. 181:1768-71.
24. Kapikian, A. Z., R. H. Mitchell, R. M. Chanock, R. A. Shvedoff, and C. E. Stewart. 1969. An epidemiologic study of altered clinical reactivity to respiratory syncytial (RS) virus infection in children previously vaccinated with an inactivated RS virus vaccine. Am. J. Epidemiol. 89:405-21.
25. Kim, H. W., J. G. Canchola, C. D. Brandt, G. Pyles, R. M. Chanock, K. Jensen, and R. H. Parrott. 1969. Respiratory syncytial virus disease in infants despite prior administration of antigenic inactivated vaccine. Am. J. Epidemiol. 89:422-34.
26. Kim, H., S. Leikin, J. Arrobio, C. Brandt, R. Chanock, and R. Parrott. 1976. Cell-mediated immunity to respiratory syncytial virus induced by inactivated vaccine or by infection. Pediatr Res 10:75-78.
27. Hancock, G. E., K. M. Heers, K. S. Pryharski, J. D. Smith, and L. Tiberio. 2003. Adjuvants recognized by toll-like receptors inhibit the induction of polarized type 2 T cell responses by natural attachment (G) protein of respiratory syncytial virus. Vaccine 21:4348-4358.
28. Chen, M., K.-F. Hu, B. Rozell, C. Orvell, B. Morein, and P. Liljestrom. 2002. Vaccination with Recombinant Alphavirus or Immune-Stimulating Complex Antigen Against Respiratory Syncytial Virus. J. Immunol. 169: 3208-3216.
29. Bendelja, K., A. Gagro, A. Bae, R. Lokar-Kolbas, V. Krulovi-Hrei, V. Drazenovi, G. Mlinaric-Galinovi, and S. Rabati. 2000. Predominant type-2 response in infants with respiratory syncytial virus (RSV) infection demonstrated by cytokine flow cytometry. Clin Exp Immunol 121:332-338.
30. Renzi, P. M., J. P. Turgeon, J. P. Yang, S. P. Drblik, J. E. Marcotte, L. Pedneault, and S. Spier. 1997. Cellular immunity is activated and a TH-2 response is associated with early wheezing in infants after bronchiolitis. J. Pediatr. 130:584-93.
31. Roman, M., W. J. Calhoun, K. L. Hinton, L. F. Avendano, V. Simon, A. M. Escobar, A. Gaggero, and P. V. Diaz. 1997. Respiratory syncytial virus infection in infants is associated with predominant Th-2-like response. Am. J. Respir. Crit. Care Med. 156:190-5.
32. Welliver, R. C. 2003. Respiratory syncytial virus and other respiratory viruses. Pediatr. Infect. Dis. J. 22:S6-10; discussion S10-2.
33. Teng, M. N., and P. L. Collins. 2002. The Central Conserved Cystine Noose of the Attachment G Protein of Human Respiratory Syncytial Virus Is Not Required for Efficient Viral Infection In Vitro or In Vivo. J. Virol. 76:6164-6171.

34. Techaarpornkul, S., N. Barretto, and M. E. Peeples. 2001. Functional analysis of recombinant respiratory syncytial virus deletion mutants lacking the small hydrophobic and/or attachment glycoprotein gene. J. Virol. 75:6825-34.

35. Teng, M. N., S. S. Whitehead, and P. L. Collins. 2001. Contribution of the Respiratory Syncytial Virus G Glycoprotein and Its Secreted and Membrane-Bound Forms to Virus Replication in Vitro and in Vivo. Virology 289:283-296.

36. Sparer, T. E., S. Matthews, T. Hussell, A. J. Rae, B. Garcia-Barreno, J. A. Melero, and P. J. Openshaw. 1998. Eliminating a region of respiratory syncytial virus attachment protein allows induction of protective immunity without vaccine-enhanced lung eosinophilia. J. Exp. Med. 187:1921-6.

37. Tebbey, P. W., M. Hagen, and G. E. Hancock. 1998. Atypical pulmonary eosinophilia is mediated by a specific amino acid sequence of the attachment (G) protein of respiratory syncytial virus. J. Exp. Med. 188:1967-72.

38. Varga, S. M., E. L. Wissinger, and T. J. Braciale. 2000. The attachment (G) glycoprotein of respiratory syncytial virus contains a single immunodominant epitope that elicits both Th1 and Th2 CD4+ T cell responses. J. Immunol. 165:6487-95.

39. Holt, P. G. 2000. Key Factors in the Development of Asthma: Atopy. Am. J. Respir. Crit. Care Med. 161:172S-175.

40. Elliott, M. B., K. S. Pryharski, R. Lerch, C. L. Parks, O. Yu, C. K. Gupta, V. B. Randolph, N. A. LaPierre, K. M. Heers Dack, T. S. Laughlin, and G. E. Hancock. 2004. Recombinant respiratory syncytial viruses lacking the C-terminal third of the attachment (G) protein are immunogenic and attenuated in vivo and in vitro. J. Virol. 78:5773-5783.

41. Wright, P. F., M. A. Gharpure, D. S. Hodes, and R. M. Chanock. 1973. Genetic studies of respiratory syncytial virus temperature-sensitive mutants. Arch Gesamte Virusforsch 41:238-47.

42. Friedewald, W. T., B. R. Forsyth, C. B. Smith, M. A. Gharpure, and R. M. Chanock. 1968. Low-temperature-grown RS virus in adult volunteers. JAMA 204:690-4.

43. Kim, H. W., J. O. Arrobio, G. Pyles, C. D. Brandt, E. Camargo, R. M. Chanock, and R. H. Parrott. 1971. Clinical and immunological response of infants and children to administration of low-temperature adapted respiratory syncytial virus. Pediatrics. 48:745-55.

44. Crowe, J. E., Jr., P. T. Bui, A. R. Davis, R. M. Chanock, and B. R. Murphy. 1994. A further attenuated derivative of a cold-passaged temperature-sensitive mutant of human respiratory syncytial virus retains immunogenicity and protective efficacy against wild-type challenge in seronegative chimpanzees. Vaccine. 12:783-90.

45. Whitehead, S. S., A. Bukreyev, M. N. Teng, C.-Y. Firestone, M. St. Claire, W. R. Elkins, P. L. Collins, and B. R. Murphy. 1999. Recombinant Respiratory Syncytial Virus Bearing a Deletion of either the NS2 or SH Gene Is Attenuated in Chimpanzees. J. Virol. 73:3438-3442.

46. Sullender, W. 1995. Antigenic Analysis of Chimeric and Truncated G Proteins of Respiratory Syncytial Virus. Virology 209:70-79.

47. Firestone, C. Y., S. S. Whitehead, P. L. Collins, B. R. Murphy, and J. E. Crowe, Jr. 1996. Nucleotide sequence analysis of the respiratory syncytial virus subgroup A cold-passaged (cp) temperature sensitive (ts) cpts-248/404 live attenuated virus vaccine candidate. Virology. 225:419-22.

48. Bukreyev, A., S. Whitehead, B. Murphy, and P. Collins. 1997. Recombinant respiratory syncytial virus from which the entire SH gene has been deleted grows efficiently in cell culture and exhibits site-specific attenuation in the respiratory tract of the mouse. J. Virol. 71:8973-8982.

What is claimed is:

1. An isolated, recombinantly-generated respiratory syncytial virus (RSV) comprising at least one alteration in the region corresponding to amino acids 151-221 of the RSV G protein, wherein the alteration is a deletion of at least amino acids 178-219, but not more than a deletion of amino acids 151-221.

2. The isolated rRSV of claim 1, wherein the deletion in the altered G protein consists of amino acids 151 to 221.

3. The isolated rRSV of claim 1, wherein the deletion in the altered G protein consists of amino acids 178 to 219.

4. An immunogenic composition comprising an isolated, recombinantly-generated respiratory syncytial virus (RSV) comprising at least one alteration in the region corresponding to amino acids 151-221 of the RSV G protein, wherein the alteration is a deletion of at least amino acids 178-219, but not more than a deletion of amino acids 151-221, together with a physiologically acceptable diluent or carrier.

5. The immunogenic composition of claim 4, wherein the deletion in the altered G protein consists of amino acids 151 to 221.

6. The immunogenic composition of claim 4, wherein the deletion in the altered G protein consists of amino acids 178 to 219.

7. A method of immunizing a vertebrate against RSV, which comprises administering to the vertebrate the immunogenic composition of claim 4.

8. The immunogenic composition of claim 4, further comprising an adjuvant.

9. A method of immunizing a vertebrate against RSV, which comprises administering to the vertebrate the immunogenic composition of claim 8.

10. An isolated, altered G protein or polypeptide of RSV, comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV.

11. The isolated, altered G protein or polypeptide of claim 10, wherein the enhanced disease is atypical pulmonary inflammation.

12. The isolated, altered G protein or polypeptide of claim 11, wherein the atypical pulmonary inflammation is pulmonary eosinophilia.

13. The isolated, altered G protein or polypeptide of claim 10, wherein the deletion consists of amino acids 151 to 221.

14. The isolated, altered G protein or polypeptide of claim 10, wherein the deletion consists of amino acids 178 to 219.

15. An immunogenic composition comprising a physiologically acceptable diluent or carrier and an isolated, altered G protein or polypeptide of RSV, comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into the immunogenic composition and administered to a vertebrate, does not induce enhanced disease upon subsequent infection of the vertebrate with RSV.

16. The immunogenic composition of claim 15, further comprising an adjuvant.

17. The immunogenic composition of claim 15, wherein the deletion in the altered G protein consists of amino acids 151 to 221.

18. The immunogenic composition of claim 15, wherein the deletion in the altered G protein consists of amino acids 178 to 219.

19. The immunogenic composition of claim 15, which further comprises isolated F protein of RSV.

20. The immunogenic composition of claim 15, which further comprises isolated M protein of RSV.

21. The immunogenic composition of claim 15, which further comprises isolated F protein of RSV and isolated M protein of RSV.

22. A method of immunizing a vertebrate against RSV, comprising administering to the vertebrate the immunogenic composition of claim 15.

23. A method of immunizing a vertebrate against RSV, comprising administering to the vertebrate the immunogenic composition of claim 16.

24. The method of claim 23, wherein the composition further comprises an immunologically effective amount of isolated RSV F protein.

25. The method of claim 23, wherein the composition further comprises an immunologically effective amount of an isolated RSV M protein.

26. The method of claim 23, wherein the composition further comprises an immunologically effective amount of an isolated RSV F protein and an immunologically effective amount of an M protein.

27. The method of claim 23, wherein the vertebrate is a seronegative human.

28. An isolated nucleic acid molecule encoding an altered G protein or polypeptide of RSV, comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV.

29. The isolated nucleic acid molecule of claim 28, wherein the deletion in the altered G protein consists of amino acids 151 to 221.

30. The isolated nucleic acid molecule of claim 28, wherein the deletion in the altered G protein consists of amino acids 178 to 219.

31. An expression vector comprising the isolated nucleic acid molecule of claim 28 operably linked to a regulatory sequence.

32. A chimeric expression vector comprising:
   a) an isolated nucleic acid molecule encoding a G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV;
   b) an isolated nucleic acid molecule encoding all or an immunogenic portion of F protein of RSV; and
   c) a regulatory sequence operably linked to both (a) and (b).

33. A recombinant host cell comprising the expression vector of claim 31.

34. A recombinant host cell comprising the expression vector of claim 32.

35. A method of producing a G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV, the method comprising maintaining the recombinant host cell of claim 33 under conditions suitable for expression of the altered G protein or polypeptide.

36. A method of producing a chimeric polypeptide comprising a G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV, and all or an immunogenic portion of F protein of RSV, the method comprising maintaining the recombinant host cell of claim 34 under conditions suitable for expression of the encoded chimeric protein.

37. An immunogenic composition comprising a physiologically acceptable diluent or carrier and an isolated nucleic acid molecule encoding a G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when expressed by the immunogenic composition upon administration to a vertebrate, does not induce enhanced disease upon subsequent infection of the vertebrate with RSV.

38. The immunogenic composition of claim 37, further comprising a transfection-facilitating agent.

39. A method of immunizing a vertebrate against RSV, comprising administering to the vertebrate a composition comprising an immunologically effective amount of an isolated, nucleic acid molecule encoding an altered G protein or polypeptide of RSV, and a transfection-facilitating agent, wherein said altered G protein or polypeptide of RSV comprises at least one alteration in the region corresponding to amino acids 151-221 of the RSV G protein, wherein the alteration is a deletion of at least amino acids 178-219, but not more than a deletion of amino acids 151-221, and where the isolated, altered G protein or polypeptide retains immunogenicity, and which isolated, altered G protein or polypeptide, when expressed by the immunogenic composition upon administration to a vertebrate, does not induce enhanced disease upon subsequent infection of the vertebrate with RSV.

40. The method of claim 39, wherein the vertebrate is a seronegative human.

41. An immunogenic composition comprising a physiologically acceptable diluent or carrier and an immunologically effective amount of a live attenuated pathogen that has inserted within it as a heterologous nucleic acid segment, a nucleic acid sequence encoding a G protein or polypeptide of RSV comprising at least one alteration in the region corresponding to amino acids 151-221 of the RSV G protein, wherein the alteration is a deletion of at least amino acids 178-219, but not more than a deletion of amino acids 151-221, such that upon administration to the vertebrate, the altered G protein or polypeptide is expressed and is immunogenic, but does not induce enhanced disease upon subsequent infection of the vertebrate with RSV.

42. The immunogenic composition of claim 41, wherein the live attenuated pathogen is an attenuated virus.

43. The immunogenic composition of claim 42, wherein the live attenuated virus is an alphavirus.

44. The immunogenic composition of claim 43, wherein the live attenuated virus is Venezuelan equine encephalitis virus (VEEV).

45. The immunogenic composition of claim 42, wherein the live attenuated virus is a non-segmented negative strand virus of the Order designated Mononegavirales.

46. The immunogenic composition of claim 45, wherein the live attenuated virus is vesicular stomatitis virus (VSV).

47. The immunogenic composition of claim 45, wherein the live attenuated virus is a parainfluenza virus.

48. The immunogenic composition of claim 45, wherein the live attenuated virus is selected from the group consisting of measles virus, mumps virus and human metapneumovirus.

* * * * *

UNITED STATES PATENT AND TRADEMARK OFFICE

CERTIFICATE OF CORRECTION

PATENT NO. : 7,666,433 B2  Page 1 of 1
APPLICATION NO. : 11/629609
DATED : February 23, 2010
INVENTOR(S) : Hancock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this

Seventh Day of December, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 707
<212> TYPE: DNA
<213> ORGANISM: respiratory syncytial virus

<400> SEQUENCE: 1

```
ggggcaaatg caaacatgtc caaaaacaag gaccaacgca ccgctaagac attagaaagg      60
acctgggaca ctctcaatca tttattattc atatcatcgt gcttatataa gttaaatctt     120
aaatctgtag cacaaatcac attatccatt ctggcaatga taatctcaac ttcacttata     180
attgcagcca tcatattcat agcctcggca aaccacaaag tcacaccaac aactgcaatc     240
atacaagatg caacaagcca gatcaagaac acaaccccaa catcctcac ccagaatcct     300 cagcttggaa tcagtccctc taatccgtct gaaattacat cacaaatcac caccatacta     360
gcttcaacaa caccaggagt caagtcaacc ctgcaatcca acagtcaa gaccaaaaac     420 acaacaacaa ctcaaacaca acccagcaag cccaccacaa aatcaaagga agtacccacc     480
accaagccca cagaagagcc aaccatcaac accaccaaaa caaacatcat aactacacta     540
atcacctcca acaccacagg aaatccagaa ctcacaagtc aaatggaaac cttccactca     600
```

```
acttcctccg aaggcaatcc aagcccttct caagtctcta caacatccga gtacccatca    660
caaccttcat ctccacccaa cacaccacgc cagtagttac ttaaaaa                  707
```

<210> SEQ ID NO 2
<211> LENGTH: 226
<212> TYPE: PRT
<213> ORGANISM: respiratory syncytial virus

<400> SEQUENCE: 2

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Ser Lys Glu Val Pro Thr Thr Lys Pro Thr Glu
145                 150                 155                 160

Glu Pro Thr Ile Asn Thr Thr Lys Thr Asn Ile Ile Thr Thr Leu Ile
                165                 170                 175

Thr Ser Asn Thr Thr Gly Asn Pro Glu Leu Thr Ser Gln Met Glu Thr
            180                 185                 190

Phe His Ser Thr Ser Ser Glu Gly Asn Pro Ser Pro Ser Gln Val Ser
        195                 200                 205

Thr Thr Ser Glu Tyr Pro Ser Gln Pro Ser Ser Pro Pro Asn Thr Pro
    210                 215                 220

Arg Gln
225
```

<210> SEQ ID NO 3
<211> LENGTH: 794
<212> TYPE: DNA
<213> ORGANISM: respiratory syncytial virus

<400> SEQUENCE: 3

```
ggggcaaatg caaacatgtc caaaaacaag gaccaacgca ccgctaagac attagaaagg    60
acctgggaca ctctcaatca tttattattc atatcatcgt gcttatataa gttaaatctt   120
aaatctgtag cacaaatcac attatccatt ctggcaatga taatctcaac ttcacttata   180
attgcagcca tcatattcat agcctcggca accacaaag tcacaccaac aactgcaatc    240
atacaagatg caacaagcca gatcaagaac acaaccccaa catacctcac ccagaatcct   300
cagcttggaa tcagtccctc taatccgtct gaaattacat cacaaatcac cccatacta    360 gcttcaacaa caccaggagt caagtcaacc ctgcaatcca acagtcaa gaccaaaaac    420
```

-continued

```
acaacaacaa ctcaaacaca acccagcaag cccaccacaa aacaacgcca aaacaaacca      480
ccaagcaaac ccaataatga ttttcacttt gaagtgttca actttgtacc ctgcagcata      540
tgcactaaat caaggaagt acccaccacc aagcccacag aagagccaac catcaacacc       600
accaaaacaa acatcataac tacactaatc acctccaaca ccacaggaaa tccagaactc      660
acaagtcaaa tggaaacctt ccactcaact tcctccgaag gcaatccaag cccttctcaa      720
gtctctacaa catccgagta cccatcacaa ccttcatctc cacccaacac accacgccag      780
tagttactta aaaa                                                        794
```

```
<210> SEQ ID NO 4
<211> LENGTH: 255
<212> TYPE: PRT
<213> ORGANISM: respiratory syncytial virus

<400> SEQUENCE: 4
```

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Thr Lys Ser Lys Glu Val Pro Thr Thr Lys Pro Thr Glu Glu Pro Thr
            180                 185                 190

Ile Asn Thr Thr Lys Thr Asn Ile Ile Thr Thr Leu Ile Thr Ser Asn
        195                 200                 205

Thr Thr Gly Asn Pro Glu Leu Thr Ser Gln Met Glu Thr Phe His Ser
    210                 215                 220

Thr Ser Ser Glu Gly Asn Pro Ser Pro Ser Gln Val Ser Thr Thr Ser
225                 230                 235                 240

Glu Tyr Pro Ser Gln Pro Ser Ser Pro Pro Asn Thr Pro Arg Gln
                245                 250                 255

```
<210> SEQ ID NO 5
<211> LENGTH: 49
<212> TYPE: DNA
<213> ORGANISM: Artificial
<220> FEATURE:
<223> OTHER INFORMATION: Forward primer for the deletion of the portion
      encoding amino acids 151-221.
```

-continued

<400> SEQUENCE: 5
cgggtaccaa ggtctcatag tttggcgttg ttttgtggtg ggcttgctg          49

<210> SEQ ID NO 6
<211> LENGTH: 49
<212> TYPE: DNA
<213> ORGANISM: Artificial
<220> FEATURE:
<223> OTHER INFORMATION: Reverse primer for the deletion of the portion
      encoding amino acids 151-221.

<400> SEQUENCE: 6
cgggtaccaa ggtctcaact aaatcaaagg aagtacccac caccaagcc          49

<210> SEQ ID NO 7
<211> LENGTH: 51
<212> TYPE: DNA
<213> ORGANISM: Artificial
<220> FEATURE:
<223> OTHER INFORMATION: Forward primer for the deletion of the portion
      encoding amino acids 178-219.

<400> SEQUENCE: 7
cgggtaccaa ggtctcatag tgcatatgct gcagggtaca aagttgaaca c        51

<210> SEQ ID NO 8
<211> LENGTH: 49
<212> TYPE: DNA
<213> ORGANISM: Artificial
<220> FEATURE:
<223> OTHER INFORMATION: Reverse primer for the deletion of the portion
      encoding amino acids 178-219.

<400> SEQUENCE: 8
cgggtaccaa ggtctcaact aaatcaaagg aagtacccac caccaagcc          49

<210> SEQ ID NO 9
<211> LENGTH: 28
<212> TYPE: DNA
<213> ORGANISM: Artificial
<220> FEATURE:
<223> OTHER INFORMATION: PCR Forward Primer for G Protein

<400> SEQUENCE: 9
agacaagcta aaattactag cgaaatca                                 28

<210> SEQ ID NO 10
<211> LENGTH: 22
<212> TYPE: DNA
<213> ORGANISM: Artificial
<220> FEATURE:
<223> OTHER INFORMATION: FAM/TAMRA Probe

<400> SEQUENCE: 10
tagactggca gttacagagg tt                                       22

<210> SEQ ID NO 11
<211> LENGTH: 26
<212> TYPE: DNA
<213> ORGANISM: Artificial
<220> FEATURE:
<223> OTHER INFORMATION: PCR Reverse Primer for G Protein

<400> SEQUENCE: 11
gttgtgcact tttggagaat attttg                                   26

-continued

```
<210> SEQ ID NO 12
<211> LENGTH: 15
<212> TYPE: DNA
<213> ORGANISM: Artificial
<220> FEATURE:
<223> OTHER INFORMATION: CpG Adjuvant Polynucleotide

<400> SEQUENCE: 12
gcatgacgtt gagct                                                    15
```